(12) United States Patent
Kincaid et al.

(10) Patent No.: US 11,622,828 B2
(45) Date of Patent: Apr. 11, 2023

(54) ACTIVELY CONTROLLED STEERABLE MEDICAL DEVICE WITH PASSIVE BENDING MODE

(71) Applicant: Canon U.S.A., Inc., Melville, NY (US)

(72) Inventors: Matthew Michael Kincaid, Medford, MA (US); Takahisa Kato, Brookline, MA (US)

(73) Assignee: Canon U.S.A., Inc., Melville, NY (US)

( * ) Notice: Subject to any disclaimer, the term of this patent is extended or adjusted under 35 U.S.C. 154(b) by 282 days.

(21) Appl. No.: 16/886,078

(22) Filed: May 28, 2020

(65) Prior Publication Data
US 2020/0375682 A1 Dec. 3, 2020

Related U.S. Application Data

(60) Provisional application No. 62/855,354, filed on May 31, 2019.

(51) Int. Cl.
*A61B 34/00* (2016.01)
*A61B 34/37* (2016.01)
(Continued)

(52) U.S. Cl.
CPC .............. *A61B 34/74* (2016.02); *A61B 34/20* (2016.02); *A61B 34/37* (2016.02); *A61B 34/71* (2016.02);
(Continued)

(58) Field of Classification Search
None
See application file for complete search history.

(56) References Cited

U.S. PATENT DOCUMENTS

| 7,828,790 B2 | 11/2010 | Griffin |
| 8,376,960 B2 | 2/2013 | Olson |

(Continued)

FOREIGN PATENT DOCUMENTS

| JP | 2002-125919 A | 5/2002 |
| JP | 2009-516574 A | 4/2009 |

(Continued)

OTHER PUBLICATIONS

Blanc, L., et al., "Flexible Medical Devices: Review of Controllable Stiffness Solutions", Actuators, 2017, vol. 6, No. 23; doi:10.3390/act6030023.

(Continued)

*Primary Examiner* — Tamara L Weber
(74) *Attorney, Agent, or Firm* — Canon U.S.A., Inc., IP Division

(57) ABSTRACT

An apparatus, method, and system for a steerable medical instrument, configured to be used in conjunction with guided tools and devices under robotically controller medical procedures, including endoscopes, cameras, cutting tools and catheters. In one embodiment, the steerable instrument includes an elongate body (100), a control wire (110) arranged in a channel (104) of the elongate body and displaceable along the channel to bend the elongate body; and a controller (320) to selectively control drive forces applied to the control wire (110) under an actively controlled mode and a passively controlled mode. In the actively controlled mode, the controller actively bends at least part of the elongate body. In the passively controlled mode, the controller (320) decreases an amount of strain or an amount of displacement of the control wire, so that the control wire becomes compliant to external forces.

25 Claims, 10 Drawing Sheets

(51) Int. Cl.
*A61B 90/00* (2016.01)
*A61B 34/20* (2016.01)
*A61B 34/30* (2016.01)

(52) U.S. Cl.
CPC .............. *A61B 34/76* (2016.02); *A61B 90/06* (2016.02); *A61B 2034/2059* (2016.02); *A61B 2034/301* (2016.02); *A61B 2090/064* (2016.02)

(56) References Cited

U.S. PATENT DOCUMENTS

| | | |
|---|---|---|
| 8,644,988 B2 | 2/2014 | Prisco et al. |
| 9,144,370 B2 | 9/2015 | Kato et al. |
| 9,931,025 B1 | 4/2018 | Graetzel et al. |
| 2006/0106295 A1 | 5/2006 | Jais et al. |
| 2007/0135803 A1 | 6/2007 | Belson |
| 2010/0280449 A1 | 11/2010 | Alvarez et al. |
| 2011/0295267 A1 | 12/2011 | Tanner et al. |
| 2013/0053866 A1 | 2/2013 | Leung et al. |
| 2013/0090529 A1 | 4/2013 | Boulais |
| 2014/0276594 A1 | 9/2014 | Tanner et al. |
| 2015/0011830 A1* | 1/2015 | Hunter ............ A61B 1/0016 600/118 |
| 2016/0067450 A1 | 3/2016 | Kowshik |
| 2016/0151122 A1 | 6/2016 | Alvarez et al. |
| 2016/0360951 A1 | 12/2016 | Hane |
| 2017/0251905 A1 | 9/2017 | Durant et al. |
| 2018/0296281 A1 | 10/2018 | Yeung et al. |
| 2018/0368929 A1 | 12/2018 | Popovic et al. |

FOREIGN PATENT DOCUMENTS

| | | |
|---|---|---|
| JP | 2013-528066 A | 7/2013 |
| WO | 2013/108776 A1 | 7/2013 |
| WO | 2015-042453 A1 | 3/2015 |
| WO | 2017/014303 A1 | 1/2017 |

OTHER PUBLICATIONS

Kim, Y., et al., "A Stiffness-Adjustable Hyperredundant Manipulator Using a Variable Neutral-Line Mechanism for Minimally Invasive Surgery." IEEE Transactions on Robotics, Apr. 2014, pp. 382-395, vol. 30, No. 2.

Loeve, A., et al., "Scopes Too Flexible . . . and Too Stiff", IEEE Pulse, Nov./Dec. 2010, pp. 26-41.

Lei, M. et al., "A Study on the Bending Mechanism of the Flexible Ureteroscope", International Conference on Control, Automation and Systems 2010, Oct. 27-30, 2010.

Chan, M. L., "Design and characterization of MEMS micromotor supported on low friction liquid bearing", Sensors and Actuators A, 2012, pp. 1-9, vol. 177.

Black, C. B., "Modeling, Analysis, Force Sensing and Control of Continuum Robots for Minimally Invasive Surgery", PhD diss., University of Tennessee, 2017.

Kato, T., et al., "Multi-section continuum robot for endoscopic surgical clipping of intracrannial aneurysms", Med Image Comput Comput Assist Interv., 2013, pp. 364-371, vol. 16, No. 1.

Song, S., et al., "Real-time shape estimation of curvilinear flexible surgical robots: methods, experiments and analysis", Sep. 2018; DOI: 10.2316/Journal.206.2018.5.206-5329.

* cited by examiner

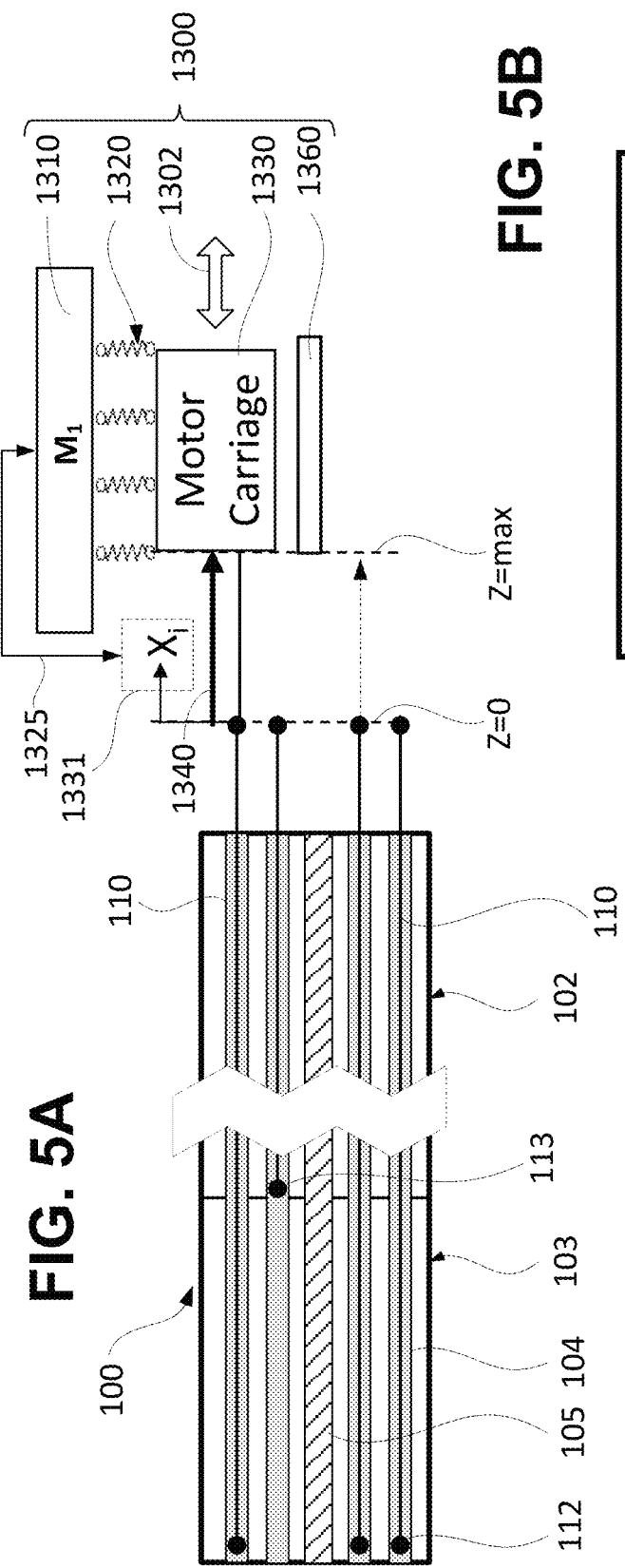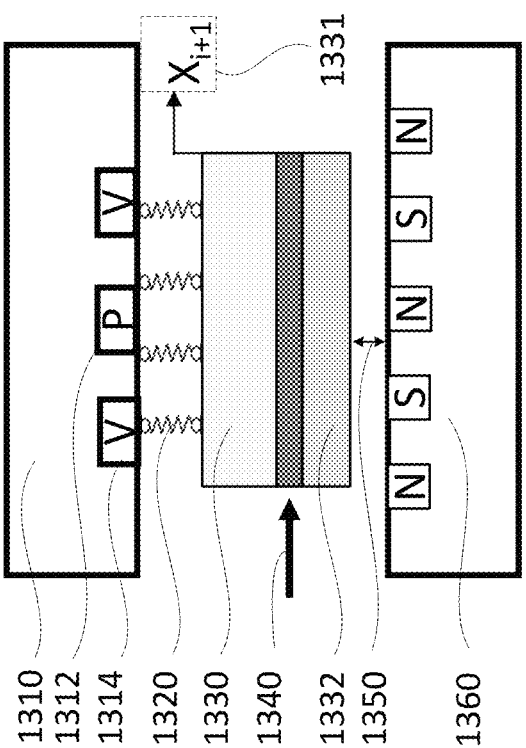
FIG. 5A
FIG. 5B

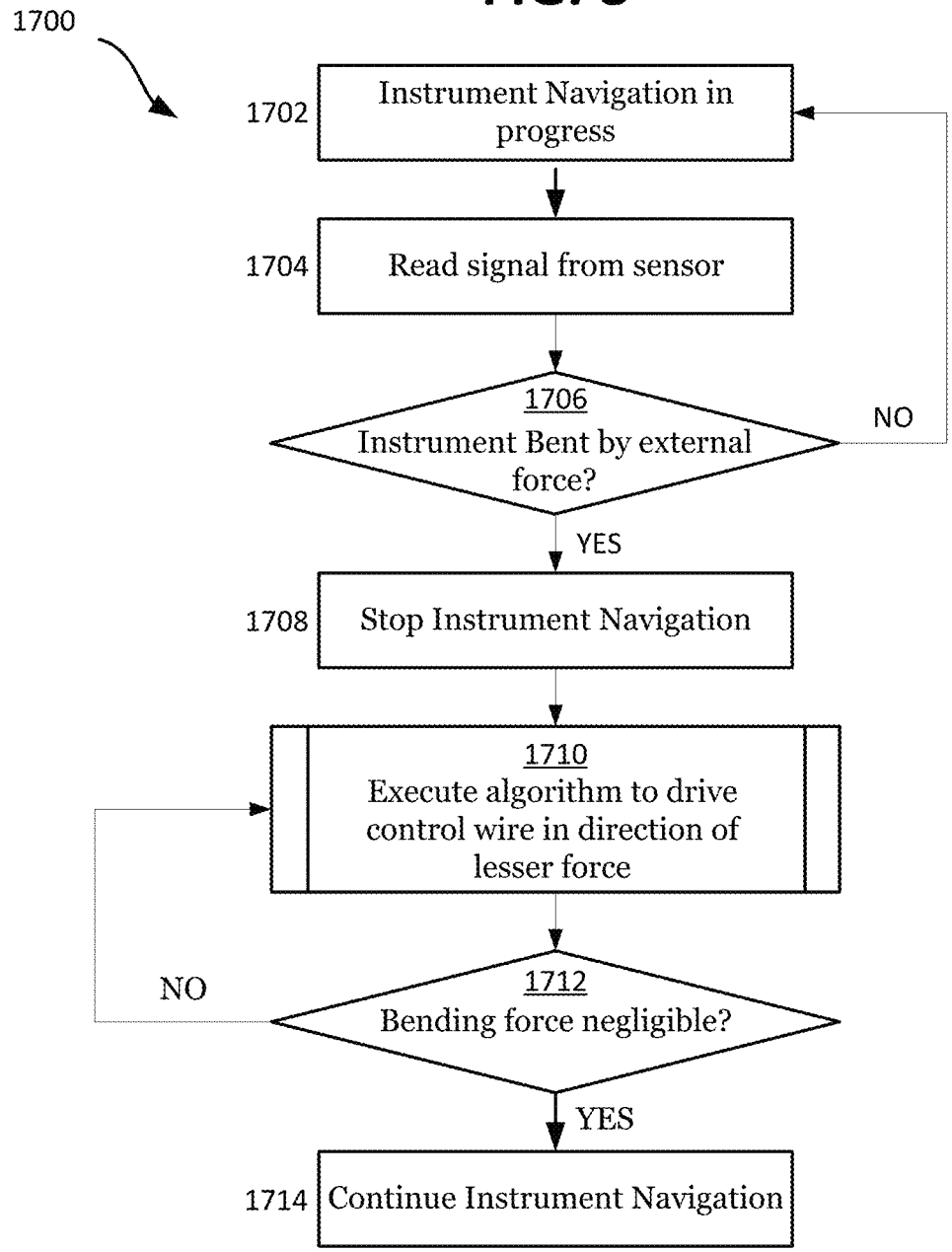

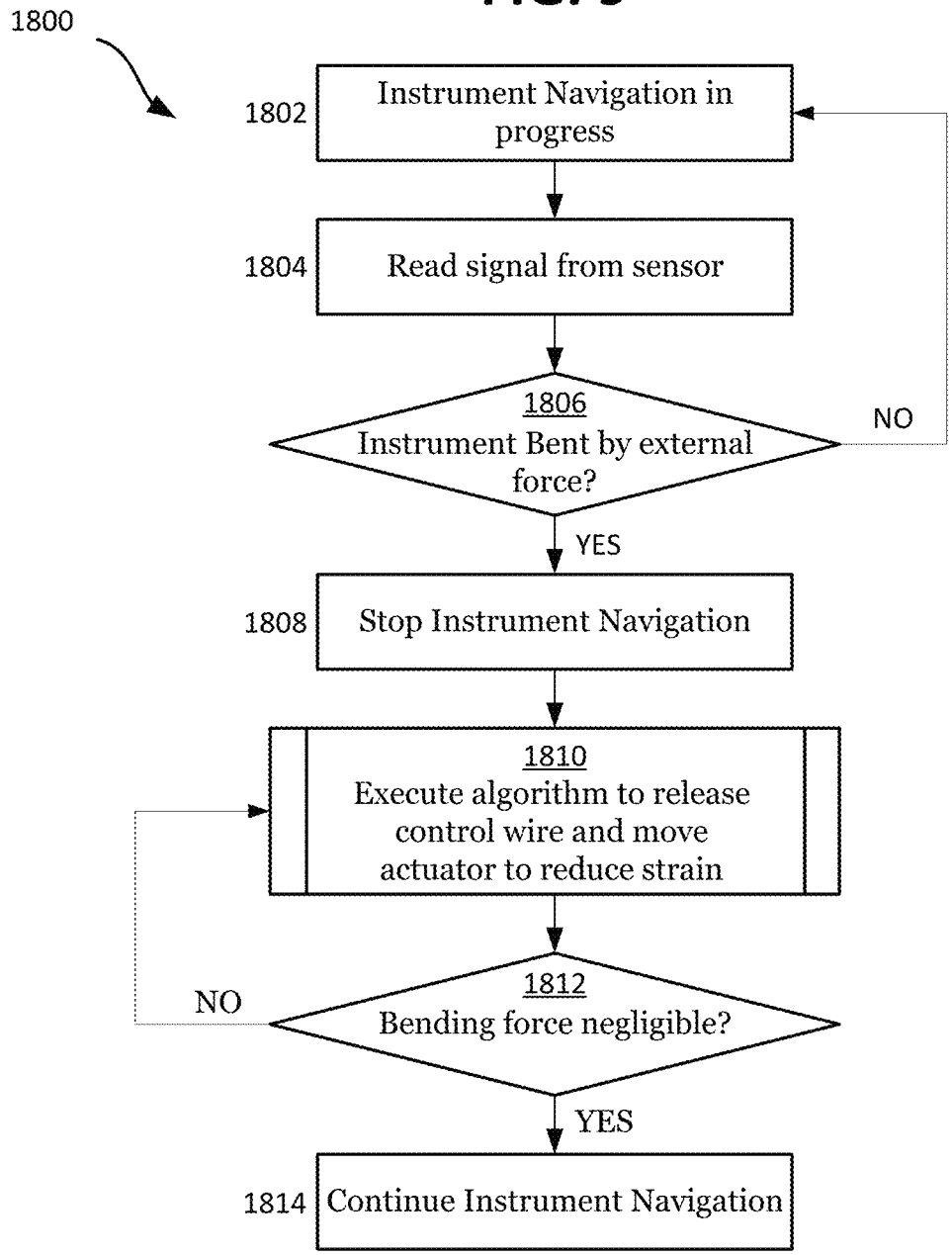

ACTIVELY CONTROLLED STEERABLE MEDICAL DEVICE WITH PASSIVE BENDING MODE

CROSS-REFERENCE TO RELATED APPLICATIONS

The present application claims priority to U.S. provisional application 62/855,354, filed May 31, 2019, the disclosure of which is incorporated by reference herein in its entirety.

BACKGROUND INFORMATION

Field of Disclosure

The present disclosure generally relates to robotic medical devices. More particularly, the present disclosure exemplifies various embodiments of an articulated steerable medical device having controllable rigidity applicable to guide interventional tools and instruments, such as robotic endoscopes and catheters, through intraluminal tortuous paths.

Description of Related Art

Bendable medical instruments such as endoscopic surgical instruments and catheters are well known and continue to gain acceptance in the medical field. These bendable medical instruments generally include an elongated flexible tube commonly referred to as a sleeve or sheath, which has an opening extending from a proximal end to a distal end. One or more tool channels extend along (typically inside) the sheath to allow access to end effectors located at the distal end of the sheath. Endoscopes may have imaging, lighting and steering capabilities at the distal end of the flexible shaft enabling navigation of non-linear lumens or tortuous pathways within the human body. This type of medical instrument is supposed to provide flexible access with at least one or more than one curve to access an intended lesion area while retaining torsional and longitudinal rigidity so that physicians can control the end effectors located at the distal end by maneuvering a proximal end of the instrument.

In minimally-invasive surgery (MIS) or natural orifice transluminal endoscopic surgery (NOTES) in which steerable medical endoscopic tools are mainly used to access difficult-to-reach intended lesion areas, some requirements of medical instrument design are (1) to minimize an outer size (outer diameter) of the bendable medical instrument, (2) to maximize the size of the opening (inner diameter) for tool channels, and (3) to provide appropriate flexibility (or rigidity) for traveling through tortuous paths without causing pain or discomfort to the patient. Therefore, to optimize the size, the bendable medical instrument must preferably include a sheath with minimal wall thickness; and to minimize patient discomfort, the bendable medical instrument must preferably have a minimum overall outer diameter. At the same time, this thin and delicate bendable medical instrument must provide sufficient rigidity and flexibility to be steerable for movement in multiple directions including insertion and retraction in a direction of its longitudinal axis, rotation about the longitudinal axis (axial rotation), and radial bending in multiple directions and/or multiple sections of the instrument. Recently, to enhance maneuverability of steerable medical instruments along intraluminal tortuous paths, robotized instruments that can control the rigidity and navigation are emerging. In known robotized instruments, to bend and create curves locally at the distal portion of a steerable instrument, different techniques have been disclosed in patent and non-patent publications.

By way of example, pre-grant patent application publication US 20160067450 A1 describes a flexible instrument with nested conduits, which provides multiple conduits to retain the shape of the proximal part, while driving tendons are bending the distal part of a bendable medical instrument. The multiple conduits would be controlled in a binary way with constrained or unconstrained proximal ends of the conduits. By selecting the constrained conduits, the bendable medical device can change the length of bending a distal segment by changing the stiffness of the bendable medical device based on the area where the conduits deploy.

Pre-grant patent application publication US 20100280449 A1 discloses a steerable instrument with multiple independent sections capable of decoupling the actuation force from portions of the steerable section in order to allow the controlled section to conform to the curvature of the pathway during insertion of the medical device. US 20100280449A1 discloses a steerable instrument with a "first portion"—which is a steerable catheter—and a "second portion"—which is a steerable sheath. Each portion is controlled independently and can be decoupled from articulation or steering forces in order to allow each portion to conform to the pathway. The first portion can then become actuated again and inserted through the second portion around the curvature of the second portion. This publication focuses on the decoupling of articulation or steering forces in a selected portion while inserting the steerable instrument through lung airways.

Pre-grant patent application publication US 20140276594 A1 discloses a robotic surgical system where a steerable instrument is controlled by control wires. The control wires are actuated by a pulley, and torque on the pulley is measured by torque sensors. The torque on the pulley is converted into control wire tension. In this publication, only tension can be sensed because the control wire can only be pulled against the pulley (i.e., pushing the control wire against the pulley would unravel the control wire from the pulley). U.S. Pat. No. 8,644,988 discloses a steerable medical instrument that uses force and feedback control to steer a medical instrument, such as a catheter with non-negligible compliance (i.e., without slack) between positioning of a distal joint and a proximal actuator.

Non-patent publications by Blanc et al., "Flexible Medical Devices: Review of Controllable Stiffness Solutions", Actuators 2017, 6, 23; doi:10.3390/act6030023, and by Loeve et al., "Scopes Too Flexible . . . and Too Stiff", Article published in IEEE Pulse, January 2011, DOI: 10.1109/MPUL.2010.939176, both describe numerous design challenges and proposed solutions for providing steerable medical devices with controllable flexibility and/or rigidity.

However, the general state of the art, in particular the exemplary publications discussed above, does not address certain situations in a typical workflow or procedure where a particular level of flexibility of the steerable instrument is desired on demand. More specifically, the known prior publications do not disclose a steerable instrument with an actively-controlled passive bending mode having zero tension on the control wires, which is desirable in certain situations.

SUMMARY OF EXEMPLARY EMBODIMENTS

According to at least one embodiment of the present disclosure, there is provided a steerable medical instrument with an actively-controlled passive bending mode. According to one aspect of the present disclosure, the steerable medical instrument comprises: an elongate body having a longitudinal axis, a proximal end, a distal end, and a plurality of channels arranged along the elongate body, the elongate body having a non-bendable section and at least one bendable section; a control wire arranged in a channel of the elongate body and extending through the non-bendable section and the at least one bendable section, the control wire fixed at the distal end of the at least one bendable section and configured to be slideable along the channel so as to bend the elongate body at an angle with respect to the longitudinal axis; a drive unit operatively connected to the control wire at the proximal end thereof; a sensor configured to output a signal indicative of an amount of strain applied to the control wire or an amount of distance displacement of the control wire; and a controller configured to cause the drive unit to selectively apply drive forces to the control wire in one of an actively controlled mode and a passively controlled mode. In the actively controlled mode, the controller uses a command signal to cause the drive unit to apply a driving force to bend the elongate body to navigate through a tortuous path. In the passively controlled mode, the controller uses the signal output from the sensor to cause the drive unit to decrease the amount of strain applied to the control wire or to decrease the amount of distance displacement of the control wire.

According to another aspect of the present disclosure, a steerable medical instrument, comprises: an elongate body (100) having a non-bendable section (102) and at least one bendable section (103), and including a plurality of channels (104, 105) extending along a longitudinal axis (Ax) from a proximal end to a distal end of the elongate body (100); a control wire (110) arranged in a first channel (104) of the elongate body (102) and extending through the non-bendable section and the at least one bendable section, and attached to the at least one bendable section; a sensor (221, 231) configured to measure an amount strain or an amount of displacement of the control wire (110); an actuator (310) mechanically coupled to the control wire (110) and configured to actuate the at least one bendable section (103) of the elongate body (100) by applying a driving force to the control wire; and a controller (320) configured to control an action of the actuator (310) according to an actively controlled mode and a passively controlled mode, based on an external force other than the driving force applied to the control wire.

According to various aspects of the present disclosure, a steerable medical device is significantly improved by providing an actively-controlled passive bending mode whereby, (1) forces in the control wires are brought to zero when maximum flexibility is needed in the steerable instrument; (2) forces and displacements of the control wires can be continually monitored regardless of the control mode employed; (3) friction in the steerable instrument is minimized even when traveling though tortuous paths; and (4) the proximal end of the control wires can freely translate while connected to it's corresponding actuator.

These and other objects, features, and advantages of the present disclosure will become apparent upon reading the following detailed description of exemplary embodiments of the present disclosure, when taken in conjunction with the appended drawings, and provided claims.

BRIEF DESCRIPTION OF DRAWINGS

Further objects, features and advantages of the present disclosure will become apparent from the following detailed description when taken in conjunction with the accompanying figures showing illustrative embodiments of the present disclosure.

FIG. 5A and FIG. 5B illustrate an exemplary embodiment of frictionless direct drive configuration implemented by an induction motor with frictionless bearings.

FIG. 8 illustrates an exemplary flowchart for implementing the actively-controlled passive bending mode of the steerable medical instrument 100 with feedback force control loop.

FIG. 9 illustrates an exemplary flowchart for implementing the actively-controlled passive bending mode of the steerable medical instrument 100 with frictionless direct drive.

DETAILED DESCRIPTION OF EXEMPLARY EMBODIMENTS

Figure 1A:
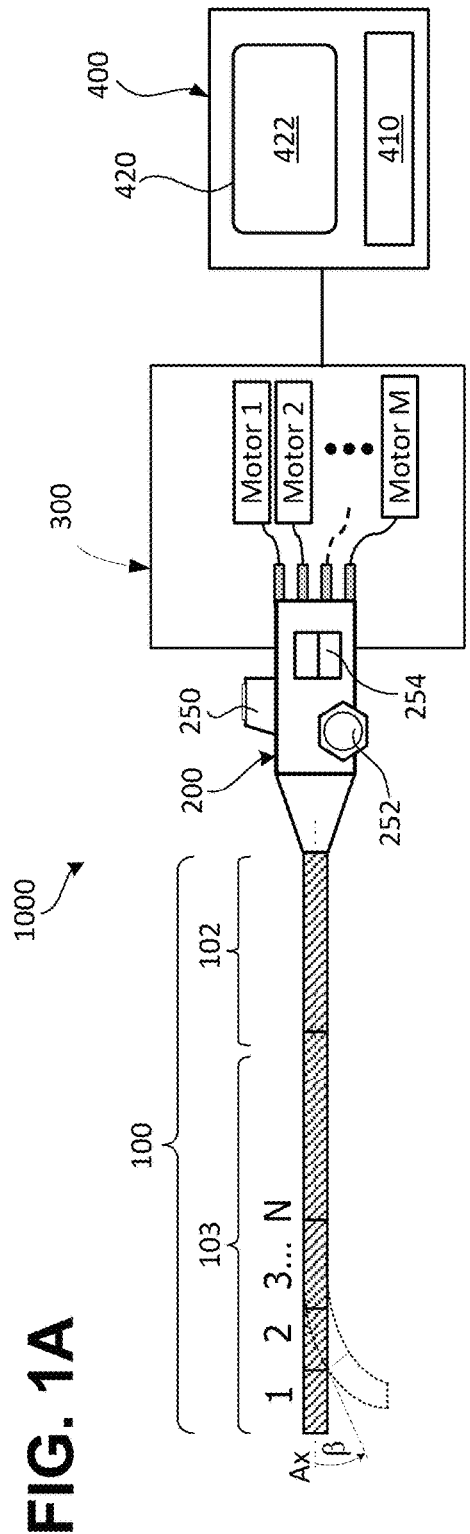
FIG. 1A illustrates an exemplary embodiment of a continuum robot system 1000 applicable to catheter- or endoscope-assisted minimally-invasive surgery (MIS) using an actively-controlled passive bending mode.

The embodiments disclosed herein are described in detail referring to the enclosed drawings. Although the drawings represent some possible configurations and approaches, the drawings are not necessarily to scale and certain features may be exaggerated, removed, or partially sectioned to better illustrate and explain certain aspects of the present disclosure. The descriptions set forth herein are not intended to be exhaustive or otherwise limit or restrict the claims to the precise forms and configurations shown in the drawings and disclosed in the following detailed description.

Throughout the figures, the same reference numerals and characters, unless otherwise stated, are used to denote like features, elements, components or portions of the illustrated embodiments. Moreover, while the subject disclosure will now be described in detail with reference to the figures, it is done so in connection with the illustrative exemplary embodiments. It is intended that changes and modifications can be made to the described exemplary embodiments without departing from the true scope and spirit of the subject disclosure as defined by the appended claims.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached", "coupled" or the like to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown in one embodiment can apply to other embodiments. It will also be appreciated by those of skill in the art that references to a structure or feature that is disposed "adjacent" to another feature may have portions that overlap or underlie the adjacent feature.

The present disclosure generally relates to medical devices, and it exemplifies various embodiments of an articulated steerable medical device having controllable rigidity applicable to guided interventional tools and instruments, such as endoscopes and catheters, through intraluminal tortuous paths. The embodiments of the present disclosure can be configured to be part of a robotic system, but those of skill in the art will appreciate that the steerable instrument disclosed herein may also be utilized in similar applications not requiring a robotic system.

The embodiments of the steerable medical instrument and portions thereof are described in terms of their state in a three-dimensional space. As used herein, the term "position" refers to the location of an object or a portion of an object in a three-dimensional space (e.g., three degrees of translational freedom along Cartesian X, Y, Z coordinates); the term "orientation" refers to the rotational placement of an object or a portion of an object (three degrees of rotational freedom—e.g., roll, pitch, and yaw); the term "posture" refers to the position of an object or a portion of an object in at least one degree of translational freedom and to the orientation of that object or portion of the object in at least one degree of rotational freedom (up to six total degrees of freedom); the term "shape" refers to a set of posture, positions, and/or orientations measured along the elongated body of the object.

As it is known in the field of medical devices, the terms "proximal" and "distal" are used herein with reference to the manipulation of an end of an instrument extending from the user to a surgical or diagnostic site. In this regard, the term "proximal" refers to the portion of the instrument closer to the user, and the term "distal" refers to the portion of the instrument further away from the user and closer to the surgical or diagnostic site.

<Configuration of Steerable Medical Device>

FIG. 1A illustrates a general structure of a continuum robot system 1000 including a computer system 400 (e.g. a console), a robotic control system 300, and a steerable instrument 100 which is connected to the control system 300 via a handle interface 200, according to one embodiment of the present disclosure. The steerable instrument 100 has a proximal non-steerable section 102 and a steerable section 103 made of multiple bending sections applicable to catheter- or endoscope-assisted minimally-invasive medical procedures. Specifically, FIG. 1A shows a robotically controlled steerable instrument 100 having the steerable section 103 divided into multiple bending segments or sections (1, 2, 3 . . . N) arranged along a longitudinal axis Ax and configured to bend at least one of the steerable sections at an angle β with respect to the longitudinal axis Ax.

The steerable instrument 100 is controlled by an actuation system comprised of a handle interface 200 and control system 300. The control system 300 generally includes a controller or is connected to a computer system 400 along with suitable software, firmware and peripheral hardware operated by a processor or central processing unit (CPU) 410, which are described later. Among other functions, the control system 300 and computer system 400 can provide a surgeon or other operator with an image display 420 and a graphical user interface (GUI) 422 to interact and operate the steerable instrument 100. The handle interface 200 provides electromechanical interconnection between the steerable instrument 100 and the control system 300. For example the handle interface 200 may provide mechanical, electrical, and/or optical connections, and a data/digital acquisition (DAQ) system for interfacing the steerable instrument 100 with the control system 300. The handle interface 200 may also provide an access port 250 to insert medical tools, one or more mechanical dials or knobs 252 that an operator can use to manually control operations of end effectors and/or steering of the instrument, and a user interface 254 having one or more control buttons and status indicators.

As part of the user interface 254, the handle 200 may include a LED for providing operational status of the robotic steerable instrument 100 to a user. In an embodiment, the LED may include, for example, different light colors for respectively indicating normal operations (green light) and abnormal operations (red light). Alternatively, the LED may include blinking codes, for example, to indicate a type of abnormal operation. In addition, the user interface 254 may include an emergency on/off switch to manually stop actuation of the steerable instrument the event of an emergency.

Figure 1B:
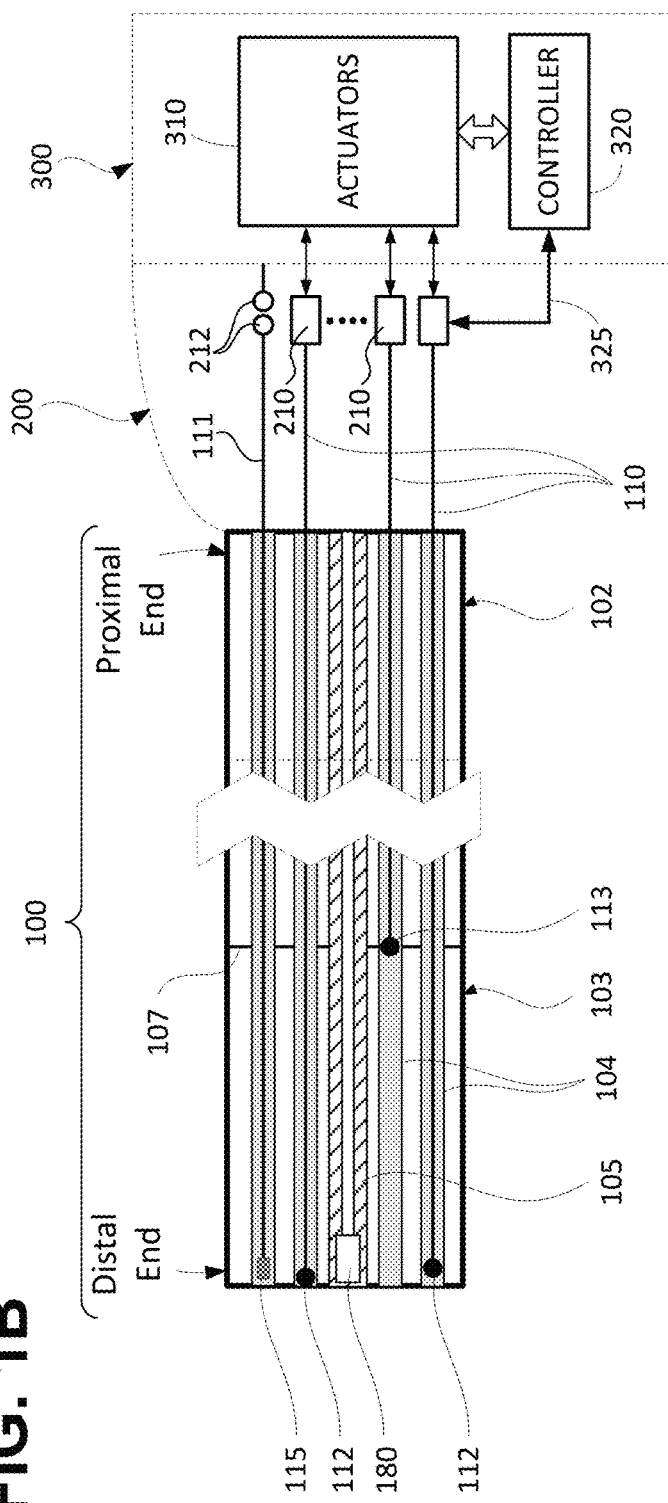
FIG. 1B illustrates in more detail a steerable instrument 100 having an elongate flexible shaft (elongate body) and a plurality of channels or openings extending from a proximal end to a distal end thereof.

FIG. 1B illustrates in more detail the steerable instrument 100 having an elongate flexible shaft (elongate body) commonly referred to as a sleeve or sheath; the sheet is formed of a non-steerable section 102 and a steerable section 103 made of multiple bending segments; one or more than one channels or openings extend from a proximal end to a distal end along the longitudinal axis Ax of the steerable instrument 100. Among the openings or channels, the sheath may include one or more tool channels 105 extending along (typically inside) the wall of the sheath, and a plurality of wire conduits 104 extending along (typically within) the wall of the sheath. The one or more tool channels 105 allow access to end effectors to be delivered or located at the distal end of the steerable section 103. The one or more channels 105 may also be used for sending or retrieving liquid or gaseous substances (e.g., air, water) to a target area, or for passing optical fibers and/or electric wires. Furthermore, the one or more channels 105 may be used for inserting a medical imaging device 180, such as an endoscope camera or a fiber-based imagining probe. An example of an endoscope camera includes, but is not limited to, a chip-on-tip (COT) camera, such as a camera with a miniature CMOS sensor arranged at the tip of the imaging device. Examples of fiber-based imaging probes include, but are not limited to, a near infrared auto-fluorescence (NIRAF) imaging probe, a spectrally encoded endoscopy (SEE) probe, an intravascular ultrasound (IVUS) probe, or an optical coherence tomography (OCT) imaging probe.

The wire conduits 104 allow anchorage and/or passage of control wires 110 used for steering (or bending) at least a section of the sheath. To that end, at the distal end of the sheath, the steerable section 103 is made of multiple bendable segments. At the proximal end of the sheath, non-steerable section 102 is connected to a grip or handle interface 200, which has one or more control wheels or knobs 252 that are used to bend the steerable section in one or more directions. The access port 250 for entrance of tolls into the tool channel 105 is also embodied in the grip or handle. The access port 250 can be used to insert small instruments, such as small forceps, needles, or electrocautery instruments and the like. In some embodiments, the wire conduits 104 can be used to pass electrical wires iii, for example, to connect electromagnetic (EM) sensors 115 to electrical terminals 212 located at the interface handle 200.

The steerable instrument 100 is configured to provide flexible access to intraluminal target areas with one or more than one bending curves to reach the intended target area near the distal end of the instrument, while retaining torsional and longitudinal rigidity so that physicians can control end effectors or imaging devices located at the distal end of the sheath by maneuvering the control system. In order to provide such steerable functionality, the steerable instrument 100 is controlled with a plurality of control wires 110 which are arranged inside wire conduits 104 along (typically inside) the wall of the sheath. Some of the control wires 110 are anchored at the distal end of the sheath using wire anchors 112, and other control wires 110 can be anchored at certain distances from the distal end using wire anchors 113. In one exemplary embodiment, a steerable instrument 100 with six control wires may have two pairs of control wires 110 (i.e., four control wires) anchored by wire anchors 113 in the midsection of the sheath (e.g., at one or more inflection points 107), and another pair of control wires 110 (two control wires) could be anchored by wire anchors 112 at the distal end of the sheath. In this manner, the steerable instrument 100 can have at least two (i.e., two or more) steerable sections controlled by 3 pairs of antagonistic control wires 110 each running through a separate conduit 104.

At the proximal end of the instrument 100, the handle interface 200 is configured to provide a mechanical linkage and an electromechanical interface between the steerable instrument 100 and the control system 300. In one embodiment, the handle interface 200 provides a plurality of electromechanical connections 210 (one connection for each of the control wires 110) so that an actuator system 310 can mechanically operate each control wire 310. A controller 320 is used to electronically control the operation of each control wire 110 based on the tension or torsional state of each control wire, as further elaborated later in this disclosure.

As shown in FIG. 1B, the control system 30o may include, as part of the actuator system 310, a plurality of actuating motors (or actuators) 1 through M, where M is an integer greater than zero and equal to the number of control wires 110. In this manner, each control wire 110 can be actively controlled by a feedback control loop 325 to implement appropriate shaft guidance for navigating through a patient's anatomy.

Figure 2A:
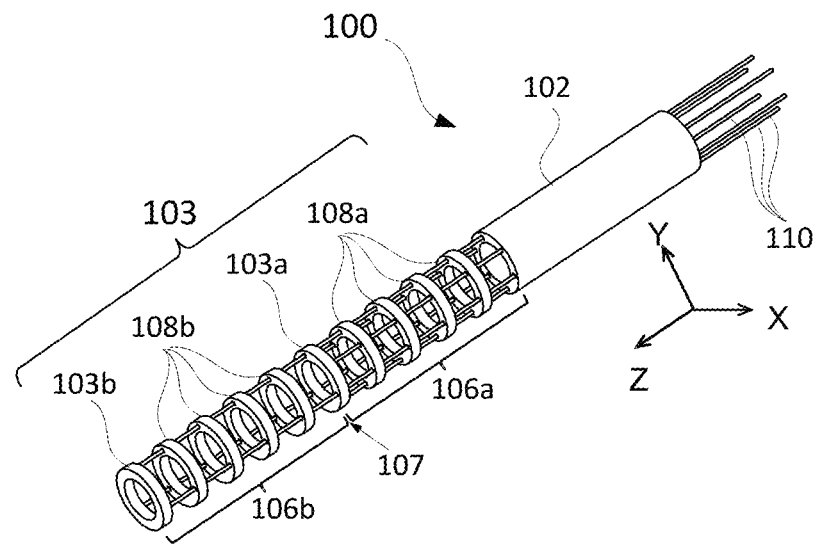
FIG. 2A is a perspective view of an exemplary steerable instrument 100 having two bending sections.

FIG. 2A is a perspective view of an exemplary steerable instrument 100. According to one embodiment, the steerable instrument 100 can be a wire-driven continuum robot, which includes a proximal non-steerable section 102 and a steerable section 103 divided into a plurality of bending segments or sections 106a and 106b with at least one inflection point 107. In the steerable instrument 100, a plurality of control wires 110 extend from the proximal end to the distal end passing through conduits 104 along the wall of non-steerable section 102 of the sheath, and through a plurality of guide members 108a, 108b, and anchor members 103a, 103b in the steerable section 103 of the sheath. The control wires 110 are arranged in a direction parallel to the Z-axis; some control wires 110 are coupled at the inflection point 107 to a first anchor member 103a, and some of the control wires 110 are coupled at the distal end to a second anchor member 103b. All control wires 110 are coupled, at the proximal end thereof, to individual motors or actuators (the actuator system 310, as shown in FIG. 1B). The control wires 110 can be metal wires, for example, piano-type wires, stainless-steel wires, or nickel-titanium-alloy wires. The anchor members 103a and 103b have an annular shape with the center axis thereof extending along the Z-axis direction. Among the plurality of control wires no, some control wires are fixedly attached to the anchor member 103a, and some control wires are attached to anchor member 103b, for example, by bonding, pinning, ultrasonic or heat welding, pressure fitting, or screws.

The support or non-steerable section 102 of the sheath has a cylindrical shape with the longitudinal axis thereof extending along the Z-axis direction and a plurality of conduits or through holes extending within the wall of the cylindrical shape. The support section is a non-steerable section and has a function of transmitting an actuating force from the actuators, when the control wires passing through the through holes of the sheath are driven in the Z-axis direction, without any buckling or slack of the control wires.

Figure 2B:
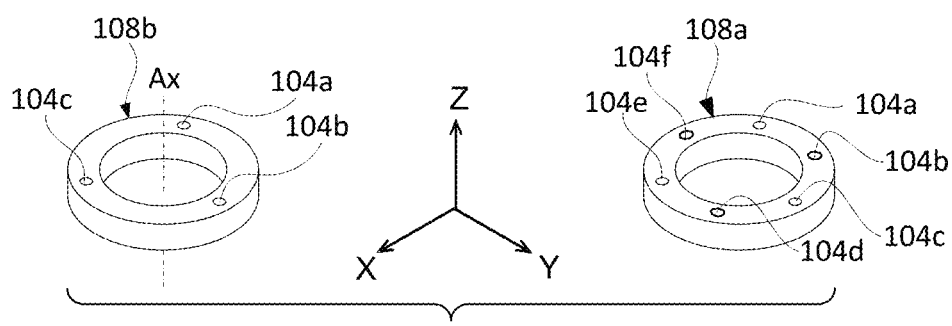
FIG. 2B shows perspective views of representative guide members with through holes (guide holes) for guiding the control wires.

FIG. 2B shows a perspective view of a representative guide member 108b and a representative guide member 108a. Each guide member has an annular shape with the center or longitudinal axis Ax extending along the Z-axis direction. The guide member 108b has wire conduits or guide holes 104a, 104b, and 104c extending along the wall of the annular shape of the guide member. The guide holes 104a, 104b, and 104c are configured to allow respective control wires 110 to pass and slide therethrough during navigation (steering) operation of the steerable instrument 100. Among the control wires 110, one control wire can be fixedly attached to a given anchor member in the inner surface of the guide hole thereof, and the other two control wires can be slideable with respect to the guide holes of that given anchor member. Since each guide member 108b contacts the control wires 110 through the guide holes 104, the guide members can include a lubricious material with a low coefficient of friction. The guide member 108a has guide holes 104a, 104b, 104c, 104d, 104e, and 104f to allow passage for the control wires 110 of the bending section 106a and bending section 106b. Similar in design to the bending section 106b, the bending section 106a has a plurality of guide members 108a and each guide member has guide holes 104a-104f. The guide holes 104a-104f are arranged to allow the control wires 110 coupled to the anchor member 103b and control wires coupled to the anchor member 103a to pass through the guide holes.

Figure 2C:
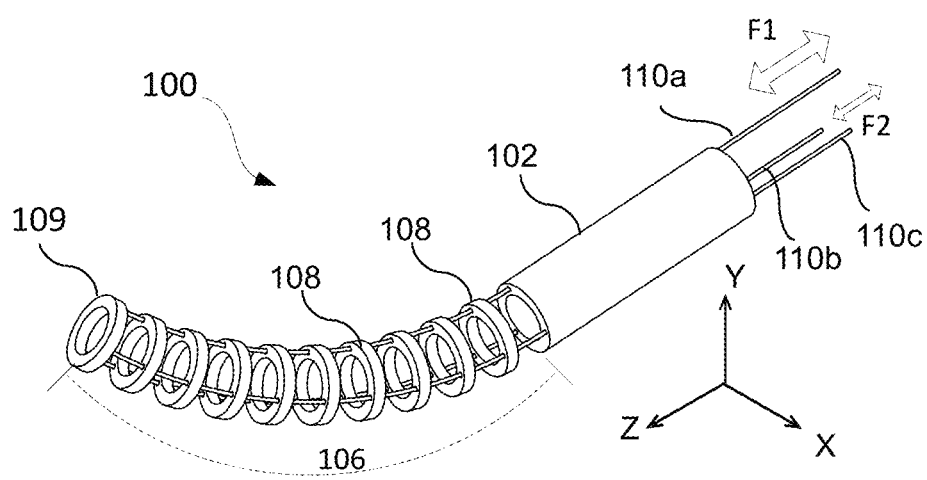
FIG. 2C shows an example of bending or steering a single bending section 106 of steerable instrument 100.

The bending motion (steering) of the steerable instrument 100 when the control wires 110 are actively driven to navigate through a tortuous path is described next. For simplicity, the bending of a single bending segment or section is explained. As shown in FIG. 2C, a single bending section 106 of steerable instrument 100 includes, from the distal end thereof, an anchor member 109, a plurality of guide members 108, and a support non-steerable section 102 with a plurality of guide holes. Control wires 110a, 110b, and 110c extend from the proximal end to the distal end of the steerable instrument along the guide holes 104a, 104b, and 104c, respectively. One or all of the control wires 110 are fixedly coupled at the distal end thereof to the anchor member 109. The control wires 110 coupled at the distal thereof to anchor member 109 are slideable with respect to the guide members 108 by the action of an actuator or motor connected at the proximal end of each control wire (refer to FIG. 1A-1B). One of the three control wires 110 (e.g., control wire 110b in FIG. 2C) is fixed (or mechanically grounded) with respect to all guide members 108, and the remaining two control wires 110 (e.g., control wires 110a and 110c in FIG. 2C) are slideable with respect to the guide holes of the guide members 108.

In bending the steerable instrument 100, each control wire 110 is individually controlled by a respective actuator or motor. For example, in FIG. 2C, while control wire 110b may be fixed or anchored to anchor member 109, control wire 110a is pulled with a first control force F1, and control wired 110c is pulled with a second control force F2 different from force F1 (control force F2 is lower than control force F1, in this example). In this manner, the bending section 106 can be bent in a desirable direction, in accordance with a combination of the driving amounts of linear displacement of control wires 110a and f10c. To control the posture of the distal end of the steerable instrument 100, driving two (or even one) of the three control wires is sufficient. As the forces F1 and F2 are applied to the control wires 110a and f10c, respectively, a corresponding sensor detects the tensile force applied thereto, as explained in more detail below. Here, it should be noted that forces F1 and F2 are not limited to tensile forces exerted by pulling the control wires. Forces F1 and F2 can also be compressive forces applied to the control wires 110 by mechanically pushing the control wires by a desired amount of compressive force.

While the case of driving the control wires anchored at the distal end of a single bending section 106 has been described above with respect to FIG. 2C, if control wires of all bending sections of FIG. 2A are driven, the postures of each bending section (1, 2, 3 . . . N) may be independently and selectively controlled to bend with a snake-like movement, depending of the driving amounts of the individual control wires driven by actuators of the actuator system 310 (drive unit). Further, a mechanism that twits or rotates the wire-driven steerable instrument 100 about its longitudinal axis may be additionally provided. In order to provide a certain amount of rotation or twisting action to the steerable instrument 100, a bending section may be first bent in a desirable direction by driving only one control wire 110 and then rotating the entire sheath by actuating a second control wire 110 in a different bending section. Such manipulation of the steerable instrument 100 can be implemented based on well known mechanical and kinematic principles, for example, as described in U.S. Pat. No. 9,144,370 which is hereby incorporated by reference herein for all purposes.

According to one embodiment, the steerable instrument 100 shown in FIG. 2A-2C may have an outer diameter of about 0.14 inches, with a distal steerable section being around 2.0 inches in length, and the total length of the instrument 100 being about 24 inches. The anchor members have conduits 104 and a tool channel 105 similar to the guide rings, and are typically constructed from medical-grade plastics or similar composites. These materials allow for fabrication of flexible, yet torsionally resilient steerable instruments, such as catheters and endoscopes of reduced dimensions. For example, other prototype dimensions for a steerable instrument 100 are about 3.3 mm outer diameter (OD), 2.4 mm inner diameter (tool channel), and about 550 mm of length.

In general, either during insertion or retraction of the steerable instrument, the center line of the lumen (e.g., an airway) is the desired trajectory to be followed during active control of the bending sections. To that end, known steerable instruments, such as robotic guided catheters or endoscopes, have attempted to implement various concepts of shaft guidance systems with the goal of forcing the flexible shaft to keep to the desired trajectory. In one example, when using a shaft guidance system, the steerable instrument is advanced through a lumen while sensors measure the insertion depth of the shaft-guide and the angulations of user-controlled steerable tip segments to obtain trajectory information. The trajectory information is stored in a memory of the system and continuously updated. After a short advance in insertion depth, the shape of the steerable shaft-guide is corrected by adjusting (rotating or bending) segments of the instrument in such a way that the new shape closely matches the desired trajectory. This process is repeated until a target area is reached. The same process is applied when the steerable instrument is withdrawn from the patient. See, e.g., US 2007/0135803, which is incorporated by reference herein for all purposes.

However, most steerable medical instruments still rely on support from the surrounding anatomy to follow the desired trajectory either during insertion or withdrawal. In particular, when external disturbances (e.g., external forces due to patient involuntary movement) are applied to the steerable instrument, it is difficult to keep the steerable instrument on the desired insertion (or withdrawal) trajectory because the tip (or other part) of the steerable instrument can become stuck on the patient's anatomy and thus hinder appropriate navigation (e.g., due unexpected bending or kinking of the instrument). Notably, during retraction of the steerable instrument, the guidance system is typically maintained inactive, which places the steerable instrument in a non-controlled (passive) state. However, the steerable instrument can still contact the patient's anatomy and unexpectedly become stuck; this can cause discomfort and/or pain to the patient. To avoid this situation, the above-referenced publication US 2007/0135803 proposes to actively control the shape of the steerable instrument using a sensor-based mapping technique that is continuously maintained as the instrument is moved within the patient.

However, when removing the steerable instrument from the pathways of a patient's anatomy, it can be beneficial to let the instrument be very flexible (e.g., with zero tension), while still maintaining the ability to actively control its rigidity at any given time. For example, letting the instrument be very flexible (compliant) during extraction causes fewer traumas to the patient's anatomy (e.g., airway, colonic wall, etc.), reduces the required force to remove the instrument, and reduces patient discomfort. However, in the event where the instrument needs to be reinserted or redirected after a partial or complete extraction (e.g., due to patient respiration or movement), it is necessary to immediately control the position and tension force of the instrument. Therefore, there is a need for an improved steerable medical instrument having (1) a minimal outer size (outer diameter), (2) maximum opening size (inner diameter) for tool channels, and (3) actively controlled flexibility (or rigidity) for efficiently traveling through tortuous paths without causing any pain or discomfort to a patient. In particular, in an event where the instrument needs to be reinserted or redirected after a partial or complete extraction (e.g., due to patient respiration or movement), it is desirable to let the instrument be very flexible (e.g., with approximately zero tension), while still maintaining the ability to control its rigidity with an actively-controlled passive bending mode.

In the present disclosure, the guidance system is controlled to place the steerable instrument 100 in a passively controlled state (actively controlled passive bending mode) such that (1) forces in the control wires 110 are brought to zero when maximum flexibility is needed in the steerable instrument; (2) forces and displacements of the control wires 110 are continually monitored regardless of the control mode employed; (3) friction in the steerable instrument is minimized even when traveling though tortuous paths during insertion or retraction; and (4) the proximal ends of the control wires 110 can freely translate while remaining actively connected to corresponding actuators.

More specifically, the present disclosure proposes a mode of passive bending which can be readily transitioned to active shape control, and vise-versa, without any loss of critical feedback information such as control wire position and control wire tension or compression force. The main principle of this passive-to-active mode conversion is that the actively controlled driving wires (control wires 110) allow for there to be negligible force applied, therefore creating a very soft bending behavior of the steerable instrument 100. This effect or mode is referred herein as an actively-controlled passive bending mode of the steerable medical device. Although the actively-controlled passive bending mode of the steerable medical device can be accomplished in a variety of configurations, it is important that the driving wires are directly driven with hardware that avoids adding friction or giving excessive slack. To that end, it is preferable to drive the control wires 110 with hardware capable of maintaining a steady and accurate relationship between the controller and the end effector, so that the position of the actuated elements is accurately controlled. The actively-controlled passive bending mode is particularly advantageous in controlling smooth and accurate bending of the steerable medical instrument during insertion and retraction through tortuous pathways of a patient's anatomy.

In any of the embodiments, there is a motor or actuator that is actuating a control wire. There can be an individual motor or actuator for each control wire, or there can be a single motor or actuator that can control various control wires individually. The control wire is moved longitudinally along the length direction of the instrument in conjunction with other control wires to create a bending moment at a distal location on the instrument. The structure of the instrument allows for one or more of these bending sections to be actuated individually. In the present disclosure, one important point is that regardless of the type of actuator used (DC motor, linear inductive motor, ultrasonic motor, or the like) a linear force is generated to move the control wires individually in the active bending mode, and a control loop is used to maintain each control wire completely passive (compliant and able to be moved by external forces, as if the wire were disconnected from any driving actuator), while still maintaining encoder position feedback, and force feedback, on the driving wires. In one embodiment, to maintain each control wire completely passive, the controller implements a force balance by reducing strain forces to substantially zero. In another embodiment, the controller implements an active movement of the actuator connected to the control wire; this is different than force balanced feedback because in this instance the actuator is able to be passively moved by the control wire.

In the case of a direct current (DC) motor, there needs to be a transformation from rotational motion to linear motion; for this, a lead screw or a ball screw mechanism is typically used. But other alternatives, such as ultrasonic and direct drive actuators, can be more advantageous. The benefit of an ultrasonic motor and of a linear inductive motor is that these are both linear actuators and do not need mechanical conversion. The ultrasonic motor or linear inductive motor can directly drive the control wire without any mechanical gears or intermediate mechanisms. One benefit of directly driving the control wire with such linear actuators is the reduction of friction and other nonlinearities (e.g. mechanical slop in a lead screw mechanism).

In an active control mode, each control wire for a given bending section is assigned a particular position. Any error in position is measured and a corrective action is taken to reduce this error. This happens many times per second and will quickly reduce the position error to a negligible amount. The result is that the commanded shape of the instrument is in closed loop control based on the control wire positions.

However, it is sometimes necessary to allow the shape of the instrument to conform to external forces applied to the instrument externally, such as the forces from a tortuous pathway wall, or the unexpected change of navigation path due to, for example, the patient's breathing movement. To apply force feedback, the present disclosure includes force sensors on each of the control wires. When tension or compression is sensed on the control wires, the controller can measure the tension or compression or control wire displacement based on the signal from the sensors. Then, an algorithm is provided to take a corrective action to reduce the measured force towards zero; this will reduce the overall forces acting between the tortuous pathway wall and the instrument. This process can also happen many times per second and can reduce forces to a negligible amount quickly.

In the present disclosure, another aspect of reducing external forces on the instrument due to contact between the instrument and a tortuous pathway is accomplished by a unique control wire configuration and actuation method. Most known steerable instruments use only tension mode in their control wires, and have at least two control wires in an antagonistic configuration for each set of actuation locations. This means that one bending section that can bend in one plane will need two control wires when only tension is used. This conventional method also requires there to be a stiff backbone in the instrument which prevents the instrument from deforming in the longitudinal direction under tension. In the present disclosure, however, it is possible to use both tension and compression in the control wires, and the steerable instrument does not have a backbone. Instead, in the present disclosure we create a pure bending moment in a bending section using multiple control wires in a symmetric configuration using force couples. A pure bending moment creates zero longitudinal force along the instrument; this allows to not only accurately control the tension and compression forces, but also to reduce the size of the instrument by not incorporating a backbone. Typically, with tension-only control wires, a small but non-zero amount of tension is kept on the control wire at all times to preload the mechanism and avoid any slack or nonlinearity that would disrupt the control system. The steerable instrument of the present disclosure does not have that issue. There is no mechanical slop or slack in the control wire; in particular when it is directly connected to the actuator; and the actuator is a linear actuator. This allows a reduction of all axial forces in the control wire to zero, while continuously monitoring and adjusting the controlling forces. This action, combined with the lack of stiff backbone, creates a very compliant instrument on demand. Moreover, the programmed algorithm seamlessly changes from the actively controlled bending mode to the passively controlled bending mode and vice versa.

<First Implementation: Force Control Loop>

Figure 3:
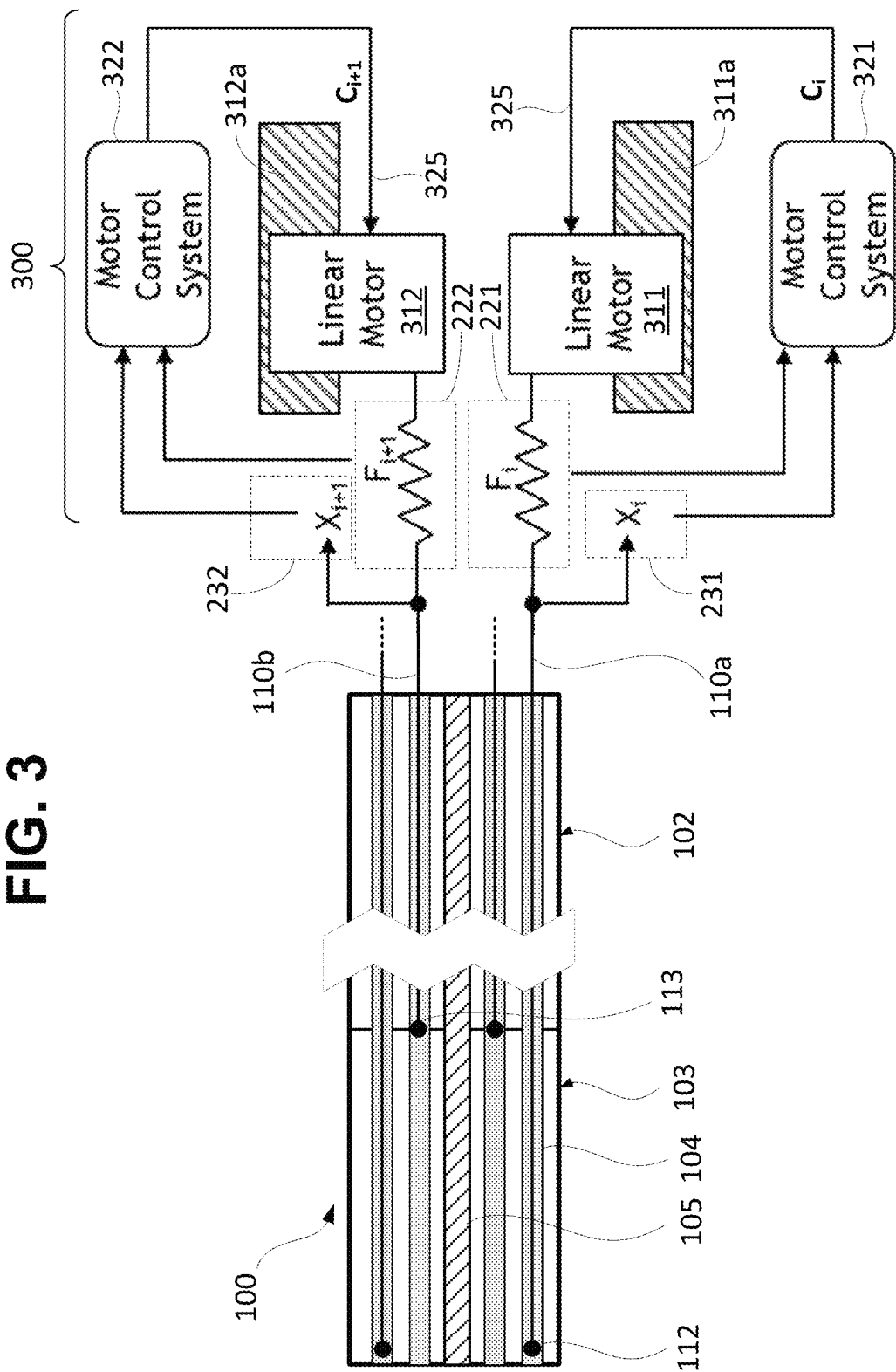
FIG. 3 illustrates an exemplary embodiment of the actively-controlled passive bending mode, which is referred herein as a "force control loop" implementation.

FIG. 3 illustrates an exemplary embodiment of the actively-controlled passive bending mode, which is referred herein as a "force control loop" implementation. As shown in FIG. 3, each control wire 110 of the steerable instrument 100 is connected at its proximal end thereof to a corresponding motor and motor control system. For ease of illustration, FIG. 3 shows a first control wire 110a connected to a first linear motor 311 which in turn is controlled by a first motor control system 321 (motor controller). Similarly, a second control wire 110b is connected to a second linear motor 312 which in turn is controlled by a second motor control system 322. To ensure accurate positioning (to avoid slack), the linear motor 311 is secured to a structural base 311a, and the linear motor 312 is secured to a similar base 312a. The base 311a/312a can be, for example, the housing or chassis of a patient interface unit (PIU), which encloses the interface 200 and at least part of control system 300. For a steerable instrument 100 having a number i through M of control wires 110, a corresponding number of i to M control motors or actuators are expected. However, it is neither expected nor necessary to provide a corresponding equal number of motor controllers. As long as each motor M is individually controlled to actuate a corresponding control wire 110, a single controller can be programmed to individually drive each one of all the motors or actuators described herein.

In the embodiment of FIG. 3, in order to implement the principle of passive-to-active mode conversion, each control wire 110 is also connected to a strain sensor and a position sensor. In FIG. 3, the first control wire 110a is connected to a strain sensor 221 and to a position sensor 231 (displacement sensor). Similarly, the second control wire 110b is connected to a strain sensor 222 and to a position sensor 232. Strain sensors can be strain-gauge based, optical based, or encoder based sensors, and position sensors can be encoder based, electromagnetic based, or Hall effect based sensors; encoder based sensors include optical encoder, magnetic encoder, potentiometer, etc.

The strain sensor detects and/or measures compressive or tensile forces F exerted in the driven control wire 110, and outputs a signal (Fi) corresponding to (indicative of) the amount of compressive or tensile force (an amount of strain) being applied to the control wire at any given point in time. Similarly, the position sensor detects a longitudinal position (or distance moved) of the control wire 110, and outputs a signal (Xi) corresponding to (indicative of) the current position of the control wire. The signals from the strain sensor and position sensor for each control wire 110 are fed into a motor control system. A control signal (Ci) is generated by the motor control system, and this signal is fed back to the motor or actuator to move the corresponding control wire no in the direction of lesser forces. That is, the control signal (Ci) generated by the motor control system is used in a feedback loop for a corresponding for a corresponding actuator or motor which moves the corresponding control wire 110 in a direction opposite to the direction of force F so as to decrease the amount of strain being applied to the control wire. This will result in negligible remaining forces in the control wire after some short amount of time t, as described below in more detail with respect to FIG. 7A-FIG. 10. In this manner, the actively-controlled driven control wires 110 allow for there to be a substantially negligible force applied to the steerable instrument 100, therefore creating a very soft bending behavior of the distal end of the instrument.

<Second Implementation: Frictionless Direct Drive>

Figure 4:
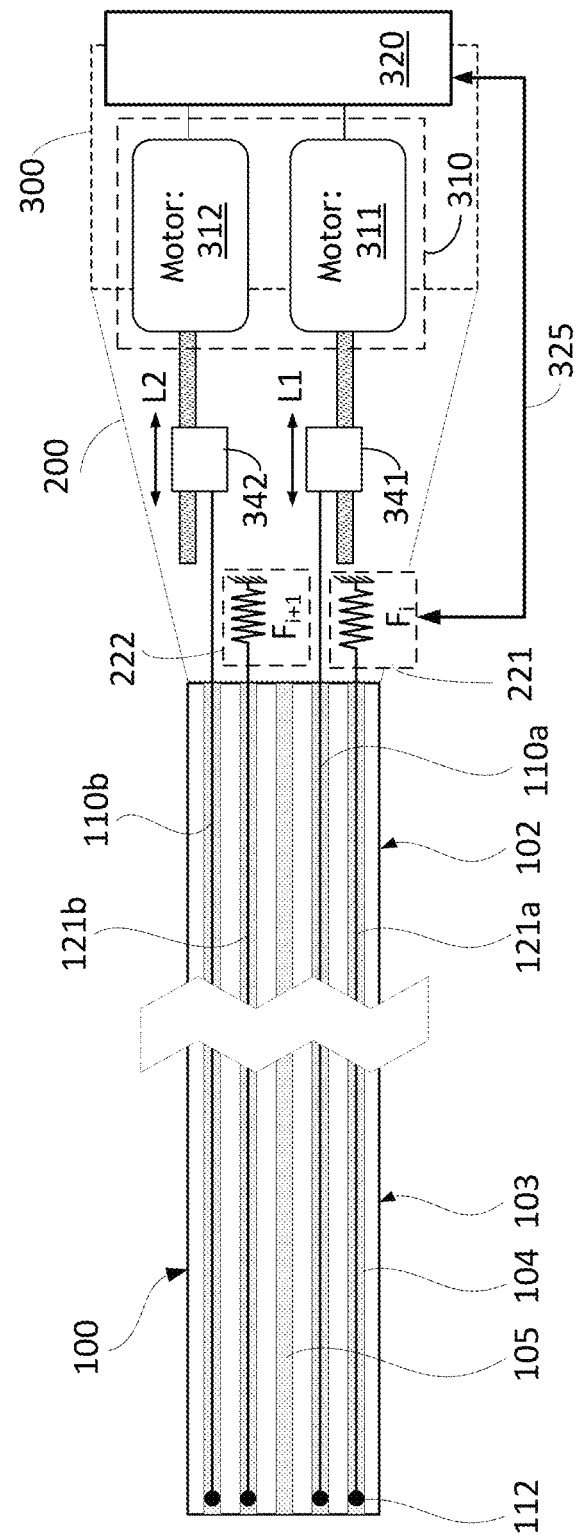
FIG. 4 illustrates an exemplary embodiment of the actively-controlled passive bending mode of a steerable instrument 100, which is referred herein as a "frictionless direct drive" implementation.

FIG. 4 illustrates another exemplary embodiment of the actively-controlled passive bending mode of a steerable instrument 100; this embodiment is referred herein as a "frictionless direct drive" implementation. In FIG. 4, a first control wire 110a of the steerable instrument 100 is directly connected at its proximal end thereof to a corresponding first motor 311 via a moving carriage 341, and a second control wire 110b is directly connected at is proximal end to a second motor 312 via a moving carriage 342. The moving carriages 341 and 342 are mechanically connected to corresponding motors 311 and 312 by, for example, screw-type linear shafts configured to displace the control wires 110 linearly along paths L1, L2. These screw-type linear actuators can be based on well known leadscrew, ball screw, or roller screw principles. Both the first and second control motors 311 and 312 are operatively connected to a motor controller 320. In addition, a first support wire 121a is connected at the proximal end thereof to a first strain sensor 211, and a second support wire 121b is connected at its proximal end to a second strain sensor 222. Each strain sensor outputs a signal corresponding to an amount of strain being applied to its nearest control wire 110 (or a signal corresponding to an average of strains forces being applied to at least two nearest control wires 110). The first strain sensor 221 output a first strain signal ($F_i$) and the second strain sensor 222 outputs a second strain signal ($F_{i+1}$). The output signal corresponding to an amount of strain detected by all strain sensors is fed back to the controller 320 as a feedback loop 325. In some embodiments, the controller 320 can be implemented with standard schemes like proportional integral derivative control (PID).

In the previous embodiment of FIG. 3, the linear motor is connected to the control wire 110 with the strain sensor being disposed therebetween. In contrast, according to the embodiment of FIG. 4, a linear motor 311/312 is directly connected from a moving carriage 341/342 to a corresponding control wire 110a/110b. In order to monitor the strain being applied to the control wire, a first strain sensor is provided at the distal end of the first support wire 121a, and a second strain sensor 222 is provided at the proximal end of the second support wire 121b. With this direct connection configuration, friction is minimized between the moving carriage 341/342 and the base (or housing) of the actuator or motor 311/312. In this manner, when the mode of the linear motor is commanded to have zero force—forces from the driving wire will displace the moving carriage 341/341 of the corresponding motor, thus eliminating residual forces or tension in the control wire.

Frictionless Direct Drive with Inductive Linear Motor and Air Bearing Stage

Another implementation of the frictionless direct drive configuration would be to use a linear inductive actuator with extremely low friction between the moving carriage and base of the actuator or motor. One example of this implementation is the use of a precision linear motor with air-bearings. Precision linear motors (PLM) with air-bearings are widely used in optical lithographic manufacturing of wafers to realize nearly zero friction and to reach submicron position accuracy for the motion of a stage. The mover of PLM is floated on the stator by three air-bearings in normal-direction and two air-bearings (one on each side) in lateral-direction. PLM with air-bearings are expected to move along a straight line and can reach submicron positioning precision during operation. The advantages of air-bearings are nearly zero friction, low heat generation, and low noise. PLM with air-bearings also greatly reduce non-linearities and disturbances caused by backlash and friction. These advantages allow the PLMs with air-bearings to be applied in advanced manufacturing fields, such as semiconductor fabrication, but could also be implemented in the frictionless direct drive configuration of control wires 110 of the novel steerable medical instrument 100 using a micro electromechanical system to operate the control wires.

FIG. 5A and FIG. 5B illustrate an exemplary embodiment of the frictionless direct drive configuration implemented by an induction motor with frictionless bearings. In FIG. 5A, the steerable medical instrument 100 is similar to the structure described previously in reference to FIGS. 1A, 1B, 3 and/or 4. In FIG. 5A, the actuator or motor is implemented as a drive unit 1300 composed of a mover or motor carriage 1330 and a stator composed of a magnetic base plate 1360, and a top plate or guide 1310. Drive unit 1300 is labeled M1 as representative of motor 1 of FIG. 1A. It is understood that a plurality of drive units 1300 (e.g., one for each control wire) are present in FIG. 5A. FIG. 5B shows in more detail a diagram of an inductive linear motor (drive unit 1300) combined with an air bearing stage. In FIG. 5B, a top plate or guide 1310 includes a plurality of pressure zones (P) 1312 and a plurality of vacuum zones (V) 1314. These zones balance each other to maintain the guide 1310 at a predetermined distance from the motor carriage 1330. The pressure and vacuum zones are preloaded by the manufacturer and are represented herein as springs to illustrate the "floating" effect of the air bearing section 1320. The mover or motor carriage 1330 is free to move in a linear direction 1302 when there is zero inductive force 1340 (no inductive force) applied to the motor carriage 1330. A position sensor 1331 monitors the linear movement of the motor carriage 1330, and outputs a signal Xi indicative of an amount of displacement of the motor carriage 1330 (moving carriage). Here, the signal Xi is used as a feedback signal 1325 to control the actuation of the motor 1300 on the control wire 110. Inductive force 1340 is applied to motor windings 1332 of the motor carriage 1330. An air gap 1350 is provided between the motor windings 1332 and permanent magnets (N, S) of a base magnetic plate 1360, which is a permanent magnet.

In this arrangement, due to the air gap 1350, the motor carriage 1330 is floating free on the air bearing. There is no friction in the longitudinal direction due to the air gap. And when no current is passed through the linear inductive motor, no force is applied to the motor carriage 1330. Therefore, movements and forces exerted on the motor carriage 1330 by a control wire 110 will cause the motor carriage to move freely in the linear direction 1302. The motion of the carriage can be continually measured by the position sensor 1331. When it is desired to actively control the position of the control wire 110 and the motor carriage 1330, the control system simply needs to pass current through the linear inductive motor and use the position data as feedback, in a control loop, as in the previous embodiments.

FIG. 5B illustrates a simple diagram of an inductive linear motor 1300 paired with a frictionless air bearing. Both elements, the bearing and the inductive drive force, are necessary for implementation of this embodiment. Here, it is necessary to have a mode where the motor carriage 1330 (which is attached to the driving control wire 110) is free to move. Then, when desired, current can be applied to the motor windings 1332, thus producing a force 1340 to move the carriage 1330 in the desired direction (preferably in a direction of lesser forces). Another component of this implementation herein is that it is possible to allow the motor carriage 1330 to move freely while maintaining positional sensor feedback. Then, at any time the mode can be switched from free-to-move mode back to actively controlled mode because the position sensor data is constantly being acquired.

One more detail about air bearings. In the diagram of FIG. 5A and FIG. 5B, the inventor has shown springs to represent the mass of air that sits between the motor carriage 1330 and the upper guide surface of top plate 1310. This particular diagram shows pressure (P) and vacuum (V) zones, in what is called a vacuum preloaded air bearing. The pressure and vacuum zones 'fight' each other. Pressure pushes the motor carriage away, and vacuum pulls it closer. The motor carriage will settle at a distance from the upper guide surface where these two opposing forces are balanced. If the distance from the motor carriage 1330 to the upper guide surface of top plate 1310 changes, the vacuum and pressure forces will be unbalanced, and a net corrective force will naturally occur which will cause the motor carriage 1330 to return to the original fly height (where the forces are balanced). This causes the control wire(s) 110 to continuously maintain a substantially zero force unless an external force is exerted thereupon.

Frictionless Direct Drive with Ultrasonic Motor

Figure 6A:
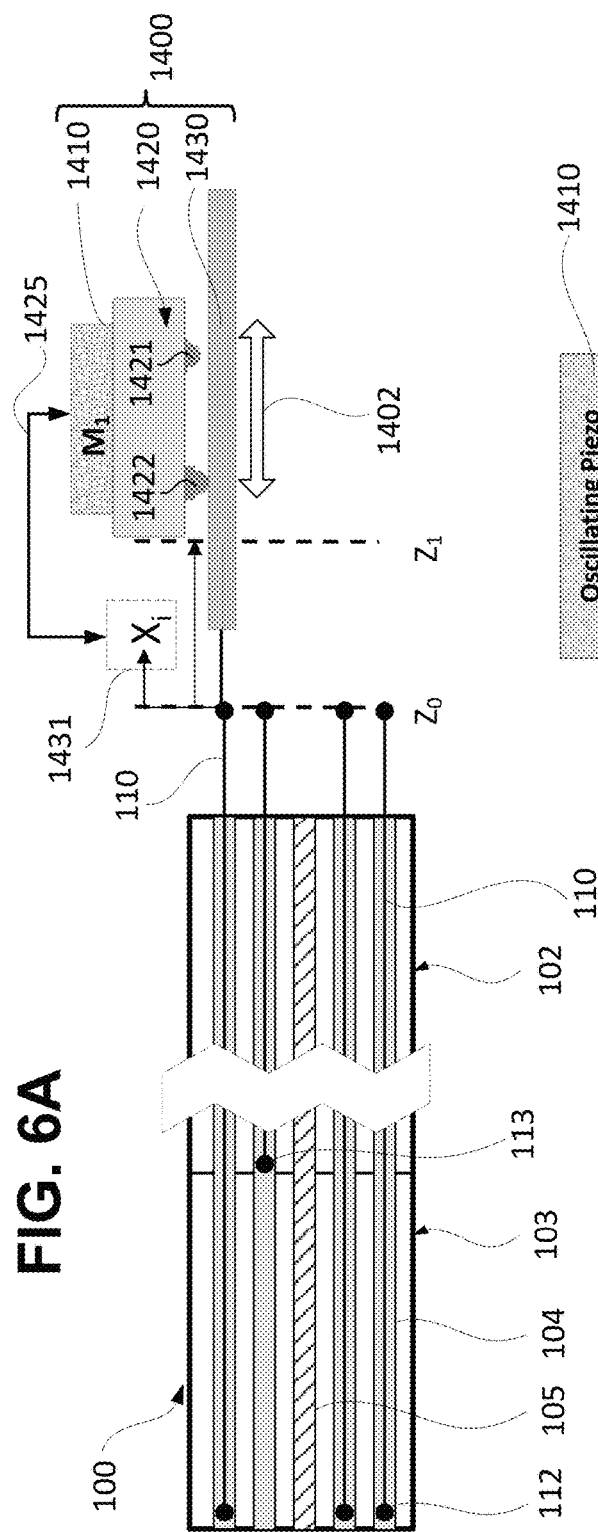
FIG. 6A, FIG. 6B, and FIG. 6C illustrate another exemplary implementation of the frictionless direct drive configuration implemented by an ultrasonic motor.
Figure 6B:
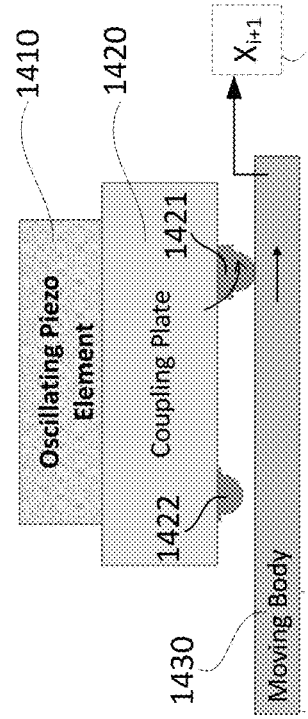
Figure 6C:
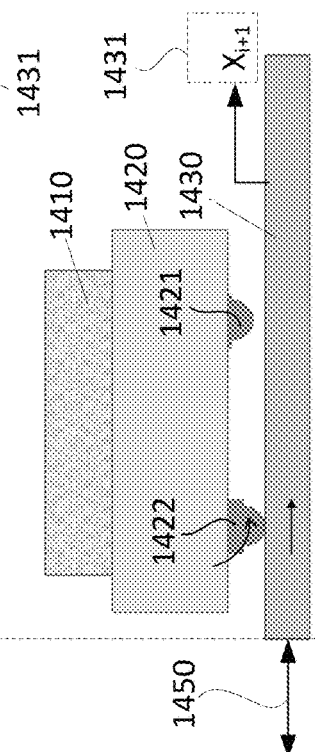

Another implementation of the frictionless direct drive configuration could be to use a linear ultrasonic motor, which can operate in a mode where the contact between the carriage and stator is very low friction due to the control signal being applied. FIG. 6A, FIG. 6B, and FIG. 6C illustrate an exemplary embodiment of an ultrasonic motor actuating on control wires 110. In FIG. 6A, the steerable medical instrument 100 is similar to the structure described previously in reference to FIGS. 1A, 1B, 3 and 4, and the bending control is similar to that described with respect to FIG. 2A-2C.

In FIG. 6A, the motor or actuator is implemented as an ultrasonic piezoelectric drive unit 1400 composed of a slider or movable body 1430 and a stator composed of a coupling plate 1420 and an oscillating piezo element 1410. Drive unit 1400 is labeled M1 as representative of motor 1 of FIG. 1A. It is understood that a plurality of drive units 1400 (e.g., one for each control wire) are present in FIG. 6A. Piezoelectric actuators are transducers that convert electrical energy into a mechanical displacement based on the piezoelectric effect. These actuators can be advantageously used as high-precision positioning mechanisms since it is possible to control small mechanical displacements at high speed, while generating relatively large forces. As an example, PILine® ultrasonic piezo motors can achieve a velocity of 500 mm/sec at a resolution of 2 nm with a holding force of up to 15 N and torque of up to 0.3 Nm.

FIGS. 6B and 6C show in more detail the application of the ultrasonic drive unit 1400 to the steerable medical device 100. In a linear ultrasonic piezo motor, a high frequency oscillating voltage waveform is applied to the piezo element 1410 under programmed control from controller system 300. The waveform signal causes modal vibration in the coupling plate 1420, and the contact points 1421 and 1422 (leer) alternately contact with the movable body 1430 at high speed. There is a normal force preload between the movable body 1430 and the feet points 1421 and 1422 which causes momentary static friction between one foot at a time and the movable body 1430 (a moving plate) while in contact. The path that the contact points take during this oscillatory vibration has components in the vertical and planar or horizontal direction. The vertical motion brings one foot at a time in contact with the plate and the horizontal motion pushes the movable body 1430 in one direction (preferably the longitudinal direction of the control wire). Similar to the previous embodiment, a strain and/or position sensor 1431 outputs as signal Xi indicative of the amount of strain or amount of displacement (distance) actuated or transferred by the movable body 1430 to the control wire no. A feedback signal 1425 is used to control actuation of the steerable instrument 100.

For example, FIG. 6B shows an initial position where the first foot 1421 contacts the movable body 1430 and causes the movable body 1430 to slide or move in the rightwards direction. FIG. 6C shows a second or final position where the second foot 1422 now contacts the movable body 1430 and causes the movable body 1430 to continue to slide or move in the rightwards direction. The resulting effect is that the movable body 1430 undergoes a linear movement of a distance 1450, while the strain sensor 1431 continuously monitors the position of the movable body 1430. In this manner, when at least one segment of the steerable section 103 of the steerable instrument 100 bends, the movable body 1430 can translate (move) linearly from a first position $Z_o$ to a second position $Z_1$ (e.g., due to catheter or endoscope bending).

Depending on the voltage waveform applied to the ultrasonic motor, different motions and behaviors can be achieved. The movable body 1430 is attached to a control wire no so that it can be driven in either direction of linear movement 1402 with a controllable speed. Position feedback is also constantly monitored by a strain sensor 1431 so that at any point in time, the control system can use the information from the strain sensor 1431 for positioning purposes. The piezo actuator also has the property that when no power is applied to the piezo actuator 1410, there is static friction between the feet and the moving body. This acts as a passive braking force on the driving control wire, which can also be useful in a clinical setting to avoid involuntary movement of an end effector. Another behavior of the ultrasonic drive unit 1400 is to have a low friction mode. A specific oscillating voltage signal can be applied to the piezo element 1410 such that the feet (contact points 1421 and 1422) create very little horizontal forces on the movable body 1430, and spend very little time in contact with the surface of the movable body 1430. The resulting effect is that the ultrasonic actuator behaves more like a low friction bearing than a friction driven actuator.

Similar to the inductive actuator design, the movable body 1430 of the linear ultrasonic motor can move freely in response to the control wire positional changes due to catheter bending. The position of the movable body 1430 is constantly monitored by the strain sensor 1431, and at any time the control system can switch back to active mode and apply forces to the moving body.

In both cases, the linear motor is directly connected to the control wire no, and is able to be moved by small forces from the control wire. Forces on the control wire and displacement of the control wire can be measured independently from each other and independently from the control mode of the motor, and these forces are not disrupted by the mode change because the strain and position sensors are continuously active even when the driving force is negligible.

When there is no force in the driving control wires no, the shape of the instrument 100 can be easily changed because the control wires are free to translate. For example, an external contact on the distal end of the steerable instrument 100 by some obstacle, such as the airway wall of a patient, can cause bending of the steerable instrument, which causes dislocation of the control wire. As soon as there is movement of the control wire, the strain sensor 1431 provides an output signal to the controller which triggers the actuator to exert a driving force on the control wire in an opposite direction (direction of lesser force).

The sensing principle for the "strain sensor" in all embodiments can be strain-gauge based. A known strain gauge is circuit which uses a force-sensing resistor used to measure compressive or tensile forces (strain) applied to an object. When an object deforms within the limit of elasticity, either it becomes narrower and longer or it becomes shorter and broadens. As a result of it, there is a change in resistance. Force-sensing resistors contain a conductive polymer film that changes its resistance in a predictable manner when force is applied on its surface. The amount of change caused to the resistance values gives the measure of the amount of force applied. Strain gauges are available in various geometries including linear strain gauges, shear strain gauges, etc. There are also semiconductor strain gauges called piezoresistors, nanoparticle strain gauges made of gold- or carbon-based resistors, and microscale strain gauges widely used in microelectromechanical systems (MEMS). In other implementations, fiber optical sensors, such as fiber Bragg gratings or Fabry-Perot interferometers can be used; see, for example, publication US 2018/0193100 which is incorporated by reference herein for all purposes.

Among the two modes of implementation, the embodiment using ultrasonic motors can be more advantageous. Specifically, due to the continuous advance in ultrasonic motor technology, it is possible to implement a steerable instrument 100 with ultrasonic motors which are of low weight; micron-sized movements, scalable for larger forces without loss of speed, and can operate independent of force and position sensing. In addition, ultrasonic motors are very small so they can be assembled in a very compact space. Larger velocities are possible to achieve without impact on amount of force delivery.

<Control System and Feedback Control Implementation>

Figure 7A:
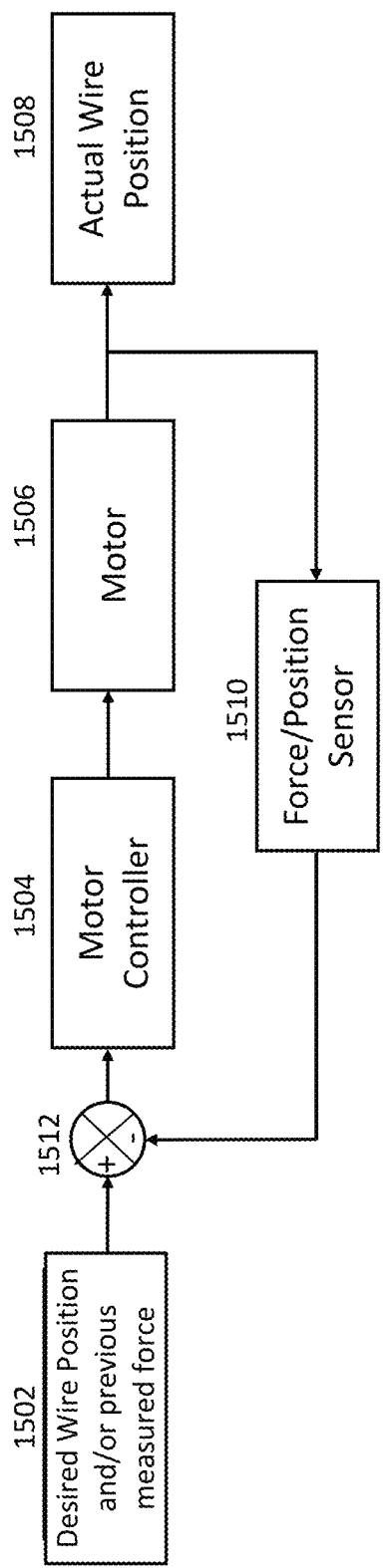
FIG. 7A illustrates an exemplary block diagram of a control system 1500 configured to implement an actively-controlled passive bending mode of the steerable medical instrument 100, according to the present disclosure.

FIG. 7A illustrates an exemplary block diagram of a control system 1500 configured to implement an actively-controlled passive bending mode of the steerable medical instrument 100, according to the present disclosure. In the actively-controlled passive bending mode, the control system 1500 controls the steerable instrument 100 such that: (1) forces in the control wires 110 are brought to zero when maximum flexibility is needed in the steerable instrument; (2) forces and displacements of the control wires 110 are continually monitored regardless of the control mode employed; (3) friction in the steerable instrument is minimized even when traveling though tortuous paths during insertion or retraction through such paths; and (4) the proximal end of the control wires 110 can freely translate while connected to it's corresponding actuator.

In FIG. 7A, the control system 1500 includes a "Desired Wire position" block 1502, a "motor controller" block 1504, a Motor or actuator block 1506, an "actual wire position" block 1508, a strain and/or position sensor block 1510, and a comparator block 1512. This control system 1500 is a very simplified version of a feedback control loop that generates an error signal (at the comparator block 1512) from a difference between the desired position and the actual position (provided by the force/position sensor block 1510). The error signal may also be generated from a comparison of a desired or previously measured force on the control wire and a sudden change in force (e.g., an external force) detected by the strain sensor. The error signal is converted by the motor controller 1504 into a control input signal which is then sent to the motor or actuator. This is a closed-loop control of one of the control wires. Each control wire 110 will have its own feedback loop (this is called Single Input Single Output "SISO"). Multiple input/output systems are also possible in this case, if more than one motor is desired to be controlled by a single feedback loop, but that implementation is not described in the present patent application.

As will be appreciated by those skilled in the art, the control system 1500 may take the form of an entirely hardware embodiment, and entirely software embodiment (including firmware, resident software, micro-code, etc.) or an embodiment combining software and hardware aspects that may all generally be referred herein as a "circuit", "module" or "system". Further, some aspects of control system 1500 may take the form of a computer program product embodied in any tangible medium of expression having computer-usable program code stored therein. For example, some aspects the control system 1500 described below with reference to flowchart illustrations and/or block diagrams of methods, apparatus (systems) and computer program products can be implemented by computer program instructions. The computer program instructions may be stored in computer-readable media that can direct a computer or other programmable data processing apparatus to function in a particular manner, such that the instructions stored in the computer-readable media constitute an article of manufacture including instructions and processes which implement the function/act/step specified in the flowchart and/or block diagram.

Figure 7B:
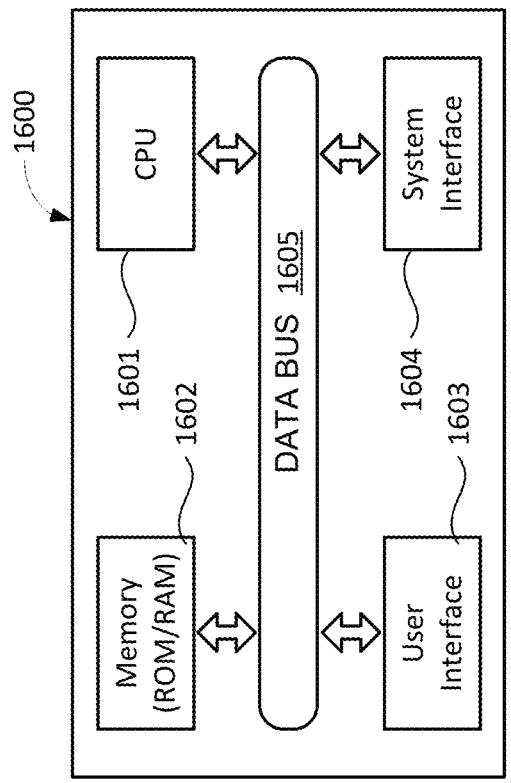
FIG. 7B illustrates functional blocks of a computer 1600 which may operate or be part of motor controller 1504 of control system 1500.

FIG. 7B illustrates functional blocks of a computer 1600 which may operate or be part of motor controller 1504 or computer system 400. As shown in FIG. 7B, the computer 1600 may include, among other things, a central processing unit (CPU) 1601, a storage memory 1602 including volatile random access memory (RAM) and non-volatile read only memory (ROM), a user input/output (I/O) interface 1603, and a system interface 1604 which are operatively interconnected via a data bus 1605. The computer 1600 can be programmed to issue a command which can be transmitted to the various parts of the control system 1600, e.g., upon receiving a user input via the user interface 1603. A touch panel screen, a key board, mouse, joy-stick, ball controller, and/or foot pedal can be included as part of the user interface 1603. Using the user interface 1603, the user can issue a command to cause the control system 1500 to actively operate the steerable instrument 100. For example, when a user inputs a command via the user interface 1603, the command is transmitted to the central processing unit CPU 1601 for execution of a given program routine thereby causing the CPU 1601 to send a command via the system interface 1604 to one or more of the control wires 110, or to ready output signals form one or more strain sensors 221 or 222.

The CPU 1601 may include one or more microprocessors (processors) configured to read and perform computer-executable instructions stored in the storage memory 1602. The computer-executable instructions may include program code for the performance of the novel processes, methods and/or calculations disclosed herein. In particular, computer-executable instructions may include program code for executing the processes illustrated in FIGS. 8, 9, 10A, and 10B to implement the actively-controlled passive bending mode of the steerable medical instrument 100.

The storage memory 1602 includes one or more computer readable and/or writable media, which may include, for example, a magnetic disc (e.g., a hard disk), an optical disc (e.g., a DVD, a Blu-ray), a magneto-optical disk, semiconductor memory (e.g., a non-volatile memory card, flash memory, a solid state drive, SRAM, DRAM), an EPROM, an EEPROM, etc. Storage memory 1602 may store computer-readable data and/or computer-executable instructions.

The system interface 1604 provides electronic communication interface to input and output devices. In particular, system interface 1604 may include one or more circuits, such as a field-programmable gate array (FPGA) to interface the computer 1600 to the motors or actuators that operate the control wires 110. The system interface 1604 may also include keyboard, a display, a mouse, a printing device, a touch screen, a light pen, an optical storage device, a scanner, a microphone, a camera, a drive, communication cable and a network (either wired or wireless).

FIG. 8 illustrates an exemplary flowchart for implementing the actively-controlled passive bending mode of the steerable medical instrument 100 with feedback force control loop. The process of FIG. 8 includes namely the steps of: (a) determining if catheter is bent by external forces; (b) reading the Tension/Compression force which is sensed by a strain or position sensor at the proximal end of the catheter; (c) executing a control algorithm to determine how to move the driving wire actuator to reduce the bending force; and (d) determining if residual bending forces on the driving wire continue to exist.

More specifically, the flow of FIG. 8 assumes the steerable instrument 100 is in an active shaft guidance mode in which, at step 1702, the control system 1500 is performing steerable instrument guidance in progress. That is, at step 1702, the system monitors the navigation of the steering instrument either during catheter insertion or during extraction (withdrawal). At step 1704, the system 1500 reads a signal from a sensor; i.e., the system reads a signal from either the strain sensor 221/222, the position sensor 231/232, or from one or more strain sensor and one or more position sensor located at the proximal end of the device. In some embodiments, strain, position, and/or orientation sensors (e.g., EM sensors 115) may also be provided at the distal end of the steerable instrument 100. At step 1706, the system 1500 continuously monitors the signal from the sensor until it makes a determination as to whether or not the steerable instrument is actuated (bent) by an external force other than the actively driving force. If the instrument is bent by an external force, YES in step 1706, the flow proceeds to step 1708. In step 1708, the system 1500 momentarily stops navigation of the steerable instrument 100. At step 1710, the system 1500 initiates an algorithm to determine how to move the motor or actuator to reduce the strain of the force being applied to the steerable device. At step 1712, the system 1500 determines if the bending force is negligible. If the force exerted by an external bending force is not negligible (NO in step 1712), the system 1500 continuously adjust the force applied to the control wire 110 until the external force becomes negligible. If the bending force is negligible (approximately equal to zero), the flow proceeds to step 1714 and the control system continues normal navigation of the steerable instrument 100.

According to one embodiment, in the process of FIG. 8, at step 1706, the system transitions from active shape control (an actively controlled mode: steps 1702-1704) to a mode of passive bending (a passively controlled mode: 1708-1712) without any loss of critical feedback information such as control wire position and control wire forces (tension or compression). To that end, the system may adopt a sensor-based mapping technique where trajectory information is stored in a memory of the system and continuously updated as the instrument moves within the anatomy of a patient, in a manner similar to that described in US 2007/0135803. However, in the present disclosure, at step 1706, when the system determines that the instrument is bent by an external force, the system enters a mode of passive bending which can easily be transitioned to active shape control, and vise-versa, without loss of critical feedback information such as control wire position and control wire forces (tension or compression). The determination at step 1706 can be based on a comparison made by the system controller between of a desired or recorded wire position (or a desired or recorded driving force on the control wire) against the actual force or position measured by the sensor. The determination at step 1706 can include a threshold value. Specifically, to prevent kinking of the steerable instrument and ensure patient comfort and safety, the user can set a threshold of the amount of linear displacement, twist, rotation (or amount strain force) in the software. For example, if the user sets a 5% or 10% or a 15% as threshold difference between desired and measured values, the system controller software triggers a change between actively controlled mode and passively controlled mode only when the error exceeds the threshold. Active transition from "active" to "passive" control of steering wires reduces the system response time without loss of critical feedback information such as control wire position and control wire forces.

FIG. 9 illustrates an exemplary flowchart for implementing the actively-controlled passive bending mode of the steerable medical instrument 100 with frictionless direct drive. The process of FIG. 9 includes namely the steps of: (a) determining if catheter is bent by external forces; (b) reading the Tension/Compression force which is sensed by the strain or position sensor at the proximal end of the catheter; (c) executing a control algorithm to place the actuator in passive mode, so that the actuator itself moves in response to the force exerted on the wire; (d) determining if bending forces on the driving control wire are negligible; and (e) returning the actuator to its active mode (engaged with the control wire).

More specifically, the flow of FIG. 9 is similar to FIG. 8 in that it assumes the steerable instrument 100 is in an active shaft guidance mode in which, at step 1802, the control system 1500 is performing steerable instrument guidance in progress. That is, in FIG. 9, steps 1802, 1804, 1806, and 1808 are similar to steps 1702, 1704, 1706, and 1708, respectively. In particular, at step 1806, the system controller determines if the steerable instrument has been bent by an external force other than the regular navigating force applied by the actuator. At step 1810, the system 150o initiates an algorithm to place the motor or actuator in a passive mode in which the actuator stops exerting any force on the control wire. In this state, if the control wire is acted upon by an external force, the actuator is displaced (moved) linearly with minimal friction until the external force being exerted on the control wire 110 becomes negligible (e.g., substantially zero). At step 1812, the system 1500 determines if the bending force is negligible. If the bending for is negligible (approximately equal to zero), the flow proceed to step 1814, and the control system 150o places the actuator in active mode (the motor engages with the control wire), and resumes normal navigation of the steerable instrument 100.

In an alternate scenario, the algorithm to release (disengage) the control wires can be based on the user's input. Specifically, at step 1806, the user may determine certain abnormal event in the instrument navigation, and manually input a signal to switch from the actively controlled mode to the passively controlled mode. For example, during navigation push issues and/or tracking issues may arise with the catheter as it is driven through tortuous paths; and when those issues occur the system can prompt the user to manually stop active navigation and enter passive control. A push issue arises when a proximal portion of a catheter is pushed further into the lumen access point, but the distal end of the catheter does not move a corresponding distance. A tracking issue arises when the proximal portion is torqued and the distal end does not rotate proportionally as expected. Pushing and tracking control are very important aspects of a catheter in navigating through difficult curves and/or obstructions in the patient's anatomy. To address these issues, the system may be equipped, for example, at the handle 200 with a warning system, such as a haptic feedback, or a sound or visual indicator to prompt the user of pushing and/or tracking issues if the instrument becomes stuck.

Figure 10A:
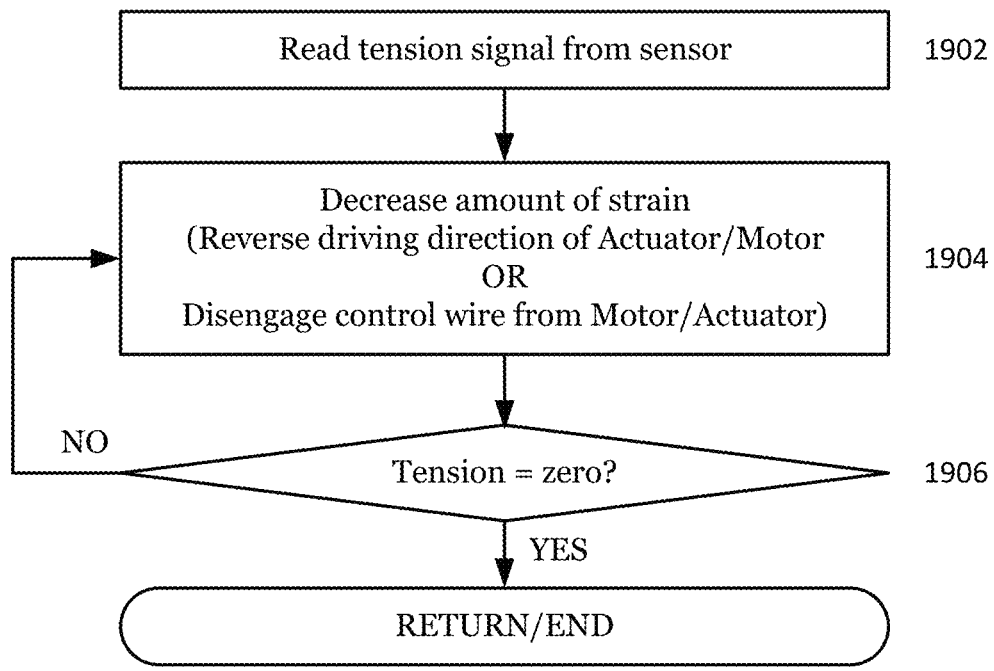
FIG. 10A illustrates an exemplary flowchart implementing an algorithm to cause the drive unit to decrease the amount of strain or compression applied to the control wire or to decrease the amount of distance displacement of the control wire so that the control wire become compliant to external forces by reducing forces in the control wire to zero when maximum flexibility is needed in the steerable instrument.

An exemplary algorithm to decrease tension on the control wire in the actively-controlled passive bending mode of the steerable medical instrument 100 may include similar processes, as discussed above with respect to FIGS. 8 and 9. FIG. 10A illustrates an exemplary algorithm which can serve equally to lower the tension force (or displacement) in step 1710 of FIG. 8 and to release the control wire in step 1810 of FIG. 9.

In FIG. 10A, the flow starts when normal navigation of the steerable instrument 100 is momentarily stopped (interrupted) due to detection of an external force exerting tension in one or more of control wires 110. That is, at step 1710 of FIG. 8 or at step 1810 of FIG. 9, the control system 1500 receives the signal from the strain or position sensor (step 1902 of FIG. 10A). In the algorithm of FIG. 10A, at step 1904, the system controller reduces the strain force measured in step 1902 by either reversing the driving direction of the actuator or motor (in the case of FIG. 8: step 1710) or by releasing the control wire (in the case of FIG. 9: step 1810). Then, in step 1906 of FIG. 10A, the system 1500 determines if the tension signal represents a strain force of approximately zero (or negligible) value. If the signal from the sensor indicates a value other than approximately zero (NO at 1906), the system continues to reduce the strain force according to either the flow process of FIG. 8 or FIG. 9 depending on whether the steerable instrument is controlled under force control loop or under frictionless direct drive. Once the tension of the external force is reduced to approximately zero (YES at 1906), the active control of tension forces ends.

Figure 10B:
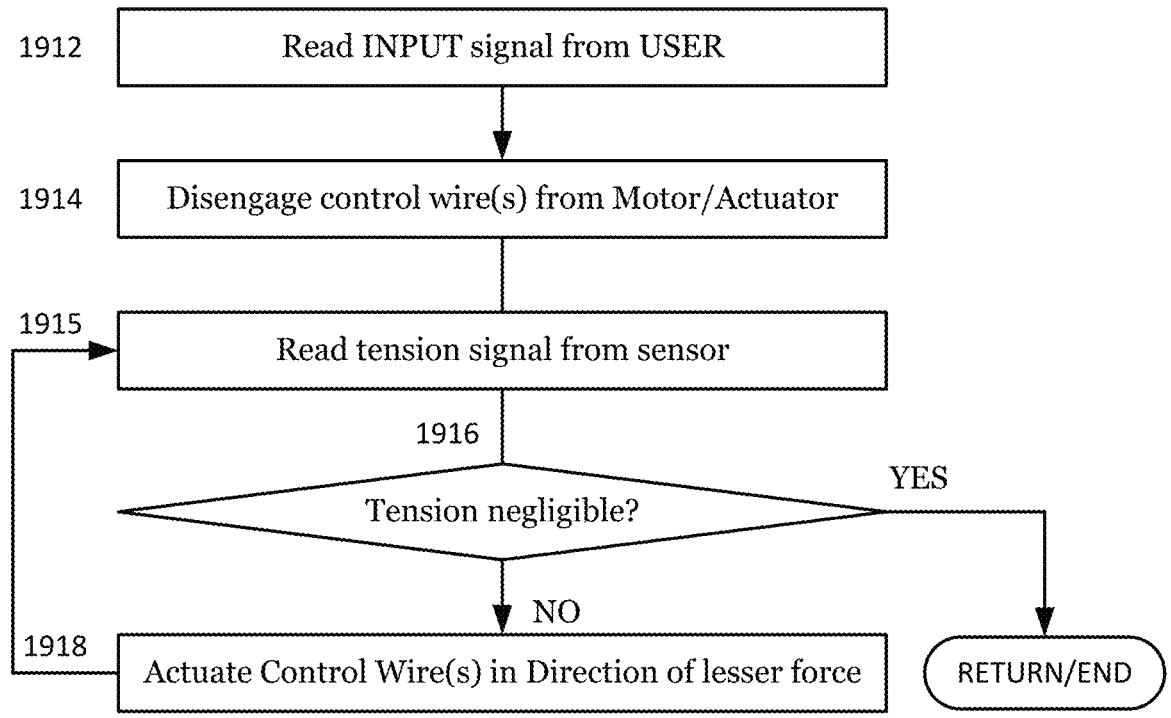
FIG. 10B illustrates an exemplary process of a scenario of user activated control to operate the steerable instrument 100 under actively controlled mode and under passively controlled mode.

FIG. 10B illustrates an exemplary algorithm which can similarly lower the tension force by releasing actuation (or adjusting displacement) of one or more control wires 110 in step 1710 of FIG. 8 or step 1810 of FIG. 9 based on a user's input. More specifically, according to description above automatic a change from an actively controlled modes to a passively controlled mode and vice versa occurs based on the external force (e.g., due patient movement) monitored by strain and/or positions sensors and certain thresholds thereof. However, in an alternative embodiment, switching between passive/active modes can also be implemented by an operator of the steerable instrument 100. In particular, the passively controlled mode might be helpful for the catheter to get out from a "blocked" situation during navigation through a tortuous anatomy (e.g., the airway) of a patient. In this case, when the physician operator determines that the catheter gets stuck, the user can switch the active mode to the passive mode by, for example, pressing a button on the controller to stop the actively controlled mode and enter the passively controlled mode. Under the passive mode, system controller makes the pose of the catheter "relaxed" and allows the catheter to get out from the "stuck" condition. After that, the operator may return the mode to the active mode, and continue to use robotic control.

FIG. 10B illustrates an exemplary process of a scenario of user activated control to operate the steerable instrument 100 under actively controlled mode and under passively controlled mode. In FIG. 10B, at step 1912, the controller 32o receives an input signal from the user, for example, when the user determines that the steerable instrument 100 may be blocked or stuck in the intraluminal pathway and presses a control button in the user interface 254 of the handle 200, or manually inputs a command through the GUI 422 of computer system 400. As soon as the user enters such input signal, at step 1914, the system controller 32o causes the actuator 310 to disengage and release the control wires 110. At step 1915, the strain sensor measures the tension force remaining in the control wires. Then, in step 1916, the system controller determines if the tension signal in the control wires is approximately zero (or negligible). If the signal from the sensor indicates a value other than approximately zero (NO at 1916), the system determines the steerable instrument is stuck, and proceeds to step 1918. At step 1918, the system actively reduces the strain force by actuating the control wire(s) 110 in a direction of lessor force. This process of steps 1915, 1916, and 1918 continues until the catheter is relaxed (in passive mode). Once the tension in control wires is reduced to approximately zero (YES at 1906), the passively controlled mode ends, and the user can return the system to the actively controlled mode.

In the actively-controlled passive bending mode, there is no active force applied to the control wires 110. When there is no force in the control wires 110, the shape of the steerable instrument 100 can be easily changed because the control wires are free to translate. For example, when external contact on the distal end of the steerable device 100 occurs by something such as the airway wall, this disturbance can cause unexpected bending of the sheath, which causes control wire dislocation and alleviates any possible discomfort or pain on the patient. In contrast, when control wires 110 are actively bent with tension force applied thereto, any external contact may not be detected and therefore could not be corrected.

In the case that the steerable instrument may accidentally get blocked or stuck in the patient's anatomy, the user can manually stop the actuation forces to place the steerable instrument in a passive related state. In addition, under manual operation, if the catheter is passive, but still stuck, the system or the user can control the actuators to drive the control wires in a direction of lesser force until the catheter becomes unstuck. After that, the operator returns the mode to the active mode, and continues to use robotic control. The passive mode by manual operation of the user is a very simple judgement for the system to perform (since operator makes judgement to switch the modes).

The actively-controlled passive bending mode results in various advantageous effects over known shaft guidance control systems. First, for both embodiments, one of the advantages is that the control wires can be completely passive (able to be moved by external forces, as if they were disconnected from any driving actuator), while still maintaining encoder position feedback, and force feedback. In addition, the control wires 110 are directly driven by a linear actuator, without gears, belts or pulleys, which can avoid adding friction and also prevents giving excessive slack to the control wires. The control wires no can be actively controlled in pull as well as push mode (tension and compression). Therefore, the actively-controlled passive bending mode can be implemented during insertion and extraction (withdrawal) of the steerable instrument 100.

A particular advantage of the second embodiment is that it is different than force balanced using feedback because in this instance the actuator is able to be passively moved by the driving wires, which is not subject to sensor noise or speed issues. In addition, friction is minimized—using a unique frequency and waveform in the case of the ultrasonic motor driven system, and by a low friction surface such as an air bearing stage in the case of the linear induction motor—to allow the motor moving body to move passively.

Although all embodiments described herein are considered to provide significant advantages over conventional techniques of active bending mode, the second embodiment is considered to be even more advantageous, in particular, when using ultrasonic motors. That is, the use of ultrasonic motors to implement the actively-controlled passive bending mode allows for a steerable instrument having low moving weight, scalable for larger forces without loss of speed. Further, it allows for the steerable instrument to operate in either the actively controlled more or the passively controlled mode independent of force and position sensing. Since ultrasonic motor technology allows for high precision control with small sized actuators, the steerable instrument can be very compact. Furthermore, without mechanical slop and with a seamless transition between active shape control and passive bending control, control at higher velocities is possible to be achieved without impact on amount of force delivery.

Modifications, Definitions, and Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like. An I/O interface can be used to provide communication interfaces to input and output devices, which may include a keyboard, a display, a mouse, a touch screen, touchless interface (e.g., a gesture recognition device) a printing device, a light pen, an optical storage device, a scanner, a microphone, a camera, a drive, communication cable and a network (either wired or wireless).

In referring to the description, specific details are set forth in order to provide a thorough understanding of the examples disclosed. In other instances, well-known methods, procedures, components and circuits have not been described in detail as not to unnecessarily lengthen the present disclosure. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

It should be understood that if an element or part is referred herein as being "on", "against", "connected to", or "coupled to" another element or part, then it can be directly on, against, connected or coupled to the other element or part, or intervening elements or parts may be present. In contrast, if an element is referred to as being "directly on", "directly connected to", or "directly coupled to" another element or part, then there are no intervening elements or parts present. When used, term "and/or", may be abbreviated as "/", and it includes any and all combinations of one or more of the associated listed items, if so provided.

Spatially relative terms, such as "under" "beneath", "below", "lower", "above", "upper", "proximal", "distal", and the like, may be used herein for ease of description to describe one element or feature's relationship to another element(s) or feature(s) as illustrated in the various figures. It should be understood, however, that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, a relative spatial term such as "below" can encompass both an orientation of above and below. The device may be otherwise oriented (rotated 90 degrees or at other orientations) and the spatially relative descriptors used herein are to be interpreted accordingly. Similarly, the relative spatial terms "proximal" and "distal" may also be interchangeable, where applicable.

The term "about" or "approximately" as used herein means, for example, within 10%, within 5%, or less. In some embodiments, the term "about" may mean within measurement error. In this regard, where described or claimed, all numbers may be read as if prefaced by the word "about" or "approximately," even if the term does not expressly appear.

The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range, if recited herein, is intended to include all sub-ranges subsumed therein.

The terms first, second, third, etc. may be used herein to describe various elements, components, regions, parts and/or sections. It should be understood that these elements, components, regions, parts and/or sections should not be limited by these terms. These terms have been used only to distinguish one element, component, region, part, or section from another region, part, or section. Thus, a first element, component, region, part, or section discussed below could be termed a second element, component, region, part, or section without departing from the teachings herein.

The terminology used herein is for the purpose of describing particular embodiments only and is not intended to be limiting. As used herein, the singular forms "a", "an", "said" and "the", are intended to include the plural forms as well, unless the context clearly indicates otherwise. It should be further understood that the terms "includes" and/or "including", when used in the present specification, specify the presence of stated features, integers, steps, operations, elements, and/or components, but do not preclude the presence or addition of one or more other features, integers, steps, operations, elements, components, and/or groups thereof not explicitly stated. It is further noted that some claims may be drafted to exclude any optional element; such claims may use exclusive terminology as "solely," "only" and the like in connection with the recitation of claim elements, or it may use of a "negative" limitation.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

While the present disclosure has been described with reference to exemplary embodiments, it is to be understood that the present disclosure is not limited to the disclosed exemplary embodiments. The scope of the following claims is to be accorded the broadest interpretation so as to encompass all such modifications and equivalent structures and functions.

The invention claimed is:

1. A steerable medical instrument, comprising:
an elongate catheter body having at least one bendable section, and including a plurality of channels extending lengthwise from a proximal end to a distal end of the elongate catheter body;
a control wire arranged in a first channel along a wall of the elongate catheter body and extending to the at least one bendable section, such that a distal end of the control wire is attached to the at least one bendable section;
a sensor configured to measure one or more of an amount strain and an amount of displacement of the control wire;
an actuator mechanically coupled to a proximal end of the control wire and configured to actuate the elongate catheter body by applying a driving force to the control wire so as to push or pull the at least one bendable section; and a controller configured to (a) control actuation of the steerable medical instrument in an active mode, (b) control compliance of the steerable medical instrument in an actively-controlled passive mode, (c) and interchangeably switch between the active mode and the actively-controlled passive mode, wherein, in the active mode, the controller controls actuation of the steerable medical instrument based on the driving force applied to the control wire by the actuator, and wherein, in the actively-controlled passive mode, the controller controls the steerable medical instrument to become compliant to an external force by reducing the driving force applied by the actuator and allowing the control wire to be moved by the external force as if the control wire were disconnected from the actuator.

2. The steerable medical instrument according to claim 1, wherein, in the actively-controlled passive mode, the controller controls the actuator itself to move in a direction opposite to the driving force applied to the control wire, such that the control wire is completely passive as if the control wire were disconnected from the actuator.

3. The steerable medical instrument according to claim 1, wherein, in the active mode, the controller controls the actuator to apply the driving force to the control wire to actively bend the elongate catheter body by displacing the control wire in a first direction, and the sensor outputs a first signal indicative of the amount strain applied to the control wire or the amount of displacement of the control wire exerted by the driving force.

4. The steerable medical instrument according to claim 3, wherein, in the actively-controlled passive mode, the controller controls the actuator to stop applying the driving force to the control wire, such that the control wire is completely passive and able to be moved by the external force as if the control wire were disconnected from the actuator.

5. The steerable medical instrument according to claim 3, wherein, in the actively-controlled passive mode, the sensor is configured to output a second signal indicative of the external force exerted on the control wire, and wherein the controller uses the second signal output from the sensor to cause the actuator to decrease the amount of strain applied to the control wire or decrease the amount of displacement of the control wire.

6. The steerable medical instrument according to claim 5, wherein, in the actively-controlled passive mode, the controller causes the actuator to reduce the driving force applied to the control wire until the amount of strain applied to control wire is negligible or until the amount of displacement of the control wire is substantially zero.

7. The steerable medical instrument according to claim 3, wherein, in the actively-controlled passive mode, the controller controls the actuator to move the control wire in a second direction opposite to the first direction, such that the control wire is completely passive as if the control wire were disconnected from the actuator.

8. The steerable medical instrument according to claim 1, wherein the sensor includes a strain gauge which measures the amount of strain on the control wire and an encoder which measures the amount of displacement of the control wire, and wherein the sensor measures the amount of strain and the amount of displacement independently from whether the controller controls the steerable medical instrument in the active mode or in the actively-controlled passive mode.

9. The steerable medical instrument according to claim 1, wherein, in the active mode, the sensor is configured to measure the amount of strain applied to the control wire by the driving force and an amount of strain applied by the external force, and wherein the controller stops the active mode and enters the actively-controlled passive mode based on the amount of strain applied by the external force becoming higher than a threshold value.

10. The steerable medical instrument according to claim 1, wherein, in the active mode, the controller is configured to receive a input signal from the user indicative of a malfunction of the steerable medical instrument, and wherein the controller stops the active mode and enters the actively-controlled passive mode based on the signal input by user.

11. The steerable medical instrument according to claim 1, wherein the actuator includes a direct drive motor which is directly coupled to the control wire.

12. The steerable medical instrument according to claim 11, wherein the direct drive motor is a linear motor directly connected to the control wire, and wherein the controller uses a command signal based on the external force to control the linear motor to exert substantially negligible force on the control wire, and wherein, when the linear motor is commanded to have substantially negligible force, the external force applied to the control wire displaces a moving carriage of the linear motor, to thereby eliminate strain forces applied to the control wire.

13. The steerable medical instrument according to claim 11, wherein the actuator includes a direct-drive unit directly coupled to the proximal end of the control wire, and wherein the controller switches between the active mode and the actively-controlled passive mode, by controlling the direct-drive unit to move freely in a linear direction substantially without friction and at least momentarily stopping the direct-drive unit in the actively-controlled passive mode.

14. The steerable medical instrument according to claim 1, wherein the actuator includes a linear ultrasonic motor having a movable carriage and stator, and wherein the controller uses the signal output from the sensor or a signal input by a user to control the ultrasonic motor to minimize contact between the movable carriage and the stator, thereby causing forces from the control wire to displace the movable carriage and eliminating strain forces applied to the control wire.

15. The steerable medical instrument according to claim 1, wherein, in the actively-controlled passive mode, the controller causes the actuator to drive the control wire to be completely passive and to be moved by the external force, as if the control wire were disconnected from the actuator, while the sensor continues to output a position feedback signal and/or a force feedback signal based on the measured amount of strain or the measured amount of displacement of the control wire.

16. The steerable medical instrument according to claim 1,
wherein, in the active mode, the at least one bendable section is configured to be driven through an intraluminal tortuous path in an insertion direction and a withdrawal direction, and
wherein, in the actively-controlled passive mode, the controller causes the actuator to drive the control wire to have substantially negligible strain in the insertion and/or withdrawal directions.

17. The steerable medical instrument according to claim 1,
wherein, in the actively-controlled passive mode, the controller causes the actuator to freely translate the control wire along the first channel without actuating the elongate catheter body while the control wire remains connected to the actuator.

18. The steerable medical instrument according to claim 1,
wherein the sensor continuously monitors an amount of strain or displacement of the control wire during both the active mode and the actively-controlled passive mode, and the controller switches between the active mode and the actively-controlled passive mode based on a difference between a desired and measured amount of strain and/or displacement of the control wire.

19. The steerable medical instrument according to claim 1,
wherein the controller automatically switches between the active mode and the actively-controlled passive mode without disconnecting the control wire from the actuator.

20. The steerable medical instrument according to claim 1,
wherein the controller automatically switches from the active mode to the actively-controlled passive mode by actively controlling the actuator to move the control wire in a direction of lesser force until the external force becomes substantially negligible, and/or
wherein, after the external force becomes substantially negligible, the controller automatically switches from the actively-controlled passive mode to the active mode by actively controlling the actuator to push or pull the control wire using the driving force.

21. The steerable medical instrument according to claim 1,
wherein the controller is further configured to switch between the active mode and the actively-controlled passive mode based on a command input by a user.

22. The steerable medical instrument according to claim 21,
wherein, upon receiving a first command input by the user, the controller switches from the active mode to the actively-controlled passive mode by releasing or stopping the driving force, or by actively controlling the actuator to move the control wire in a direction of lesser force until the strain measured by the sensor becomes substantially negligible, and
wherein, when the strain measured by the sensor becomes substantially negligible, the controller to switch from the actively-controlled passive mode to the active mode upon receiving a second command input by the user.

23. The steerable medical instrument according to claim 1,
wherein the actuator includes a rotary motor and a rotation-to-linear conversion mechanism,
wherein the rotation-to-linear conversion mechanism is directly coupled to the proximal end of the control wire so that the control wire can be controlled, in the active mode, by applying the driving force in a push direction as well as in a pull direction.

24. The steerable medical instrument according to claim 23,
wherein, in the actively-controlled passive mode, the rotary motor drives the control wire via the rotation-to-linear conversion mechanism in a direction opposite to the push direction or opposite to the pull direction so at to reduce an amount strain on the control wire, while the sensor continuously measures the one or more of strain and displacement of the control wire.

25. The steerable medical instrument according to claim 1,
wherein the actuator includes a linear ultrasonic actuator that has a holding force and is directly coupled to the proximal end of the control wire, and
wherein the controller switches between the active mode and the actively-controlled passive mode, by controlling the linear ultrasonic actuator to at least momentarily release the holding force and move the control wire in a linear direction without the driving force, while the sensor continuously measures the one or more of strain and displacement of the control wire.

\* \* \* \* \*